United States Patent [19]

Evangelista et al.

[11] Patent Number: 4,772,563

[45] Date of Patent: Sep. 20, 1988

[54] 1,10-PHENANTHROLINE DERIVATIVES AND USE IN FLUORESCENCE IMMUNOASSAYS

[75] Inventors: Ramon A. Evangelista, Scarborough; Alfred Pollak, Toronto, both of Canada

[73] Assignee: HSC Research Development Corporation, Toronto, Canada

[21] Appl. No.: 763,642

[22] Filed: Aug. 8, 1985

Related U.S. Application Data

[63] Continuation-in-part of Ser. No. 708,435, Mar. 4, 1985, abandoned.

[30] Foreign Application Priority Data

Aug. 13, 1984 [GB] United Kingdom ............... 8420521

[51] Int. Cl.$^4$ .................. G01N 33/53; C07D 471/04
[52] U.S. Cl. ................... 436/518; 436/546; 436/547; 436/800; 436/805; 544/342; 546/88
[58] Field of Search ............... 544/342; 546/88; 436/546, 800, 518, 547, 805

[56] References Cited

U.S. PATENT DOCUMENTS

| 3,338,906 | 8/1967 | Dwyer | 546/88 |
|---|---|---|---|
| 3,389,143 | 6/1968 | Halpern | 546/88 |
| 3,426,026 | 2/1969 | Ennis | 546/88 |
| 4,374,120 | 2/1983 | Soini et al. | 436/540 |
| 4,637,988 | 1/1987 | Hinshaw | 436/546 |
| 4,699,978 | 10/1987 | Barton | 546/88 |

FOREIGN PATENT DOCUMENTS

| 0002963 | 7/1979 | European Pat. Off. |
| 0068875 | 1/1983 | European Pat. Off. |

OTHER PUBLICATIONS

Leif, R. C., et al., "Development of Instrumentation and Fluorochromes for Automated Multiparameter Analysis of Cells", Clin. Chem., 23/8, 1492–1498, (1977).

Sinha, A. P. B., "Fluorescence and Laser Action in Rare Earth Chelates", Spectroscop. Inorg. Chem., 2, 255, (1971).

Bhaumik, M. L. et al., "Stroboscopic Time-Resolved Spectroscopy", Rev. Sci. Instr., 36, 37, (1965).

Bhaumik, M. L., "Mechanism and Rate of the Intramolecular Energy Transfer Process in Rare-Earth Chelates", J. Chem. Phys., 42, 747, (Jan. 1965).

Bhaumik, M. L. et al., "Fluorescence Quantum Efficiency of Rare-Earth Chelates", J. Opt. Soc. Am., 54, 1211, (Oct. 1964).

Gillard, R. D. et al., "Optically Active Co-ordination Compounds. Part XX. Reactions of 1,10-Phenanthroline Co-ordinated to Cobalt", J. Chem. Soc. (A), 1970, 1447.

Dickeson, J. E. et al., "Derivatives of 1,10-Phenanthroline-5,6-Quinone", Aust. J. Chem., 1970, 23, 1023–7.

Chandler, C. J. et al., "Synthesis of Some 2,9-Disubstituted-1,10-Phenanthrolines", J. Heterocyclic Chem., 18, 599, (1981).

Newkone, G. R. et al., "α-Methyl Functionalization of Electron-Poor Heterocycles", J. Orgn. Chem., 1983, 48, 5112–5114.

Substituted 1,10-*Phenanthrolines, XII. Benzo and Pyrido Derivatives,* Emil Koft & Francis H. Case, Department of Chemistry, Temple University, Journal of Organic Chemistry, pp. 865–868, vol. 27, 1962.

Substituted 1,10-*Phenanthrolines, VI. Chloro Derivatives,*

(List continued on next page.)

*Primary Examiner*—Robert J. Warden
*Assistant Examiner*—Robert Benson
*Attorney, Agent, or Firm*—Ridout & Maybee

[57] ABSTRACT

1,10-phenanthroline-2,9-dicarboxylic acid and novel derivatives thereof such as 4,7-diphenyl-1,10-phenanthroline-2,9-dicarboxylic acid and 4,5,9,14-tetraaza-(1,2,3,4)-dibenzanthracene-3,5-dicarboxylic acid can be coupled to proteins through coupling groups to form conjugates which form higly fluorescent chelates in the presence of lanthanide salts. Derivatives of the above acids reactive toward proteins can be readily manufactured by relatively simple synthetic routes, and are useful in fluorescent immunoassay.

29 Claims, 3 Drawing Sheets

OTHER PUBLICATIONS

Francis H. Case, Sigmund Catino & Frank Scholnic, Department of Chemistry, Temple University, *Journal of Organic Chemistry*, pp. 31–36, vol. 19, 1954.

*The Synthesis of Certain 4–Mono– and 4,7–Dihydroxy–1,-10–Phenanthrolines*, Case, Department of Chemistry, Temple University, *Journal of Heterocyclic Chemistry*, vol. 7, pp. 647–649, 1970.

*Substituted 1,10–Phenanthrolines. VII. Synthesis of Certain Phenanthrolines for Use in the Detection of Cu(I)*[1], Francis Case & James Brennan, Chemistry Department, Temple University, *Journal of Organic Chemistry*, vol. 19, pp. 912–922, 1954.

*Substituted 1,10–Phenanthrolines. IX. Cycloalkeno Derivatives*, Francis Case, Chemistry Department of Temple University, *Journal of Organic Chemistry*, vol. 21, pp. 1069–1071, 1956.

*Synthesis of Certain Polyalkyl Quinolines and 1,10–Phenanthrolines*, K. C. John & Francis H. Case, Chemistry Department, Temple University, vol. 13, No. 4, Journal of Chemical and Engineering Data, Oct. 1968, pp. 568–570.

*The Synthesis of Polymethylquinolines and 1,10–Phenanthrolines* (1), Case & Wisneski, Department of Chemistry, Temple University, *Journal of Heterocyclic Chemistry*, vol. 5, pp. 789–792, 1968.

*Substituted 1,10–Phenanthrolines. XIII. The Synthesis of New 4–Mono– and 4,7–Dialkyl– and –aryl–1,10–Phenanthrolines*, Case & Strohm, Chemistry Department, Temple University, *Journal of Organic Chemistry*, vol. 27, pp. 1641–1643, 1962.

*Substituted 1,10–Phenanthrolines. X. Ethyl Derivatives*, Case, Jacobs, Cook & Dickstein, Department of Chemistry of Temple University, *Journal of Organic Chemistry*, vol. 22, pp. 390–393, 1957.

*Substituted 1,10–Phenanthrolines. VIII. 2– and 2–Phenyl Derivatives*, Case & Sasin, Department of Chemistry, Temple University, *Journal of Organic Chemistry*, vol. 20, pp. 1330–1336, 1955.

J. R. Geigy, *2,9–Dimethyl–1,10–Phenanthroline*. Chemistry Abstract, vol. 48, 1953, 7644.

Monsanto Chemicals (Australia) Ltd., *1,10–Phenanthroline Derivatives*, Chemical Abstract, vol. 63, 1965, 11518.

Chemical Abstracts, 63:11519d, (1965).
Chemical Abstracts, 69:10426g, (1968).
Chemical Abstracts, 78:124565t, (1973).
Chemical Abstracts, 79:105229r, (1973).
Chemical Abstracts, 79:105230j, (1973).
Chemical Abstracts, 80:95912n, (1974).
95913p, *1,10–Phenanthroline Derivatives*, vol. 80, 1974, Chemical Abstracts, p. 412.

*Advances in Heterocyclic Chemistry*, Lindsay A. Summers, Academic Press, vol. 22, 1978, The Phenanthrolines, pp. 1–69.

*Heterocyclic Compounds*, Robert C. Elderfield, John Wiley & Sons, Inc., 1961, Phenanthrolines, Chapter 4, pp. 344–383.

*A Review of Fluoroimmunoassay and Immunofluorometric Assay*, D. S. Smith, Mohammad Hal-Hakiem and J. Landon, Ann. Clin. Biochem., 1981; 18:253–274.

1,10-PHENANTHROLINE DERIVATIVES AND USE IN FLUORESCENCE IMMUNOASSAYS

This application is a continuation-in-part of application Ser. No. 708,435 filed Mar. 4, 1985, abandoned.

This invention relates to reagents for fluorescent assay and more especially to novel markers which can be attached to protein for purposes of fluorescent labelling such as used in immunoassay methods, and to immunoassay methods using the novel markers.

Radio-immunoassay (RIA) methods have been used for some years, but there are hazards involved in handling, storage, and disposal of radioactive materials and there has been growing opposition against the use of radioisotopes in some countries. Furthermore, there are disadvantages associated with radioimmunoassays methods, such as the short shelf life of $^{125}I$-labelled antibodies and antigens (6–24 weeks) arising from the short half-life of $^{125}I$ (60 days) and this necessitates frequent radioiodinations and often requires disposal of unused outdated reagents. This increases the cost per test associated with RIAs for the end user. The various drawbacks and disadvantages have led to the current trend to replace radioimmunoassays (RIAs) with nonisotopic methods, the most important of which are enzyme immunoassay (EIA) and fluorescent immunoassay (FIA).

Although EIAs have found wide applicability recently, there is great concern about their sensitivity and reproducibility. In some cases, there is uncertainty about the choice of end point which should be chosen for the enzymatic reaction after the addition of substrate. The measurement of the enzyme activity (rate constant) is a more reliable method but this prolongs the assay and adds to its cost by requiring more sophisticated computational hardware. The high sensitivity of enzymatic activity to temperature difference is also a source of imprecision. Another major source of error is the presence in serum of enzymes which have effects similar to the one employed for labeling or of enzyme inhibitors which would have the opposite effect.

In current fluorescent immunoassays, immunoreactive proteins, i.e. antibodies, antigens or haptens are tagged covalently with a fluorescent label such as fluorescein, various rhodamines, dansyl chloride, or umbelliferone and the increase or decrease of fluorescence due to the immunological reaction is measured. Generally, the sensitivity of FIAs which employ these labels is lower than that of RIAs because of Rayleigh and Raman scattering and interference due to fluorescent substances such as proteins and bilirubin in serum. The scattering problem is partly overcome with the use of dedicated filter systems.

The underlying problem with fluorescent labels of current general use is their small Stokes shift (the difference between the wavelengths of the absorbed, stimulating radiation and of the emitted, fluorescent radiation, respectively) and their short fluorescent lifetimes which are comparable with those of interfering substances in serum. For example, fluorescein has absorption and emission maxima at 490 nm and 520 nm, respectively, and a fluorescence lifetime of only 5 nanoseconds.

Recently, the use of lanthanide chelates, especially those of europium, has been suggested as a way of eliminating background fluorescence to increase immunoassay sensitivity, for example in U.S. Pat. No. 4,374,120 issued Feb. 15, 1983 in the name Soini et al. The wavelengths of the absorption and emission maxima for these systems depend on the chelating ligands but the Stokes shifts are typically at least 200 nm and the fluorescence lifetimes are in the order of 100 microseconds. Background fluorescence can be eliminated completely with the use of time-resolved fluoresence immunoassay, for example by using of a gated fluorometer wherein a time delay between a pulsed excitation and detection of emission removes short-lived fluorescence due to interfering fluorochromes.

Lanthanide chelates have the unique characteristic of absorbing light to give a high yield of linelike emission with long fluorescence lifetimes. The emission results from intramolecular energy transfer from the lowest ligand triplet states to the metal ion, as reported by M. L. Bhaumik and M. A. El-Sayed, *J. Chem. Phys.*, 42, 787–788 (1965). Time-resolved spectroscopy of europium chelates using a stroboscopic technique was performed by Bhaumik and co-workers in 1965, M. L. Bhaumik, G. L. Clark and L. Ferder, *Rev. Sci. Inst.*, 36 37–40 (1965).

Although the fluorescent chelates of lanthanides, as described for example in the above-mentioned U.S. Pat. No. 4,374,120, provide acceptable results in fluorescence spectroscopy analysis, the chelates of this patent are difficult to manufacture as their preparation requires a multi-step process which is difficult and complex to commercialize.

We have now found that certain novel 1,10-phenanthroline derivatives form lanthanide chelates which fluoresce in aqueous solution, and which may be employed in fluorescent immuno- and other assays. These derivatives can be readily manufactured by relatively simple procedures.

We have found that the known compound 1,10-phenanthroline-2,9-dicarboxylic acid of the formula

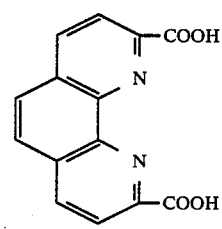

is a ligand which forms chelates with lanthanide salts which are highly fluorescent in aqueous solution. Further, as explained in more detail below, we have found various novel derivatives of the above acid form lanthanide chelates of like fluorescent capabilities. In some cases, the molecular structure of these derivatives enhances and advantageously modifies their radiation-absorbing and fluorescent radiation-emitting characteristics. These derivatives include compounds containing one or more functional groups that are capable of coupling covalently with proteins, or one or more groups readily convertible to such functional groups, and which are useful as markers for conducting fluorescent immuonassay.

Broadly, the invention comprises reagents for fluorescent assay comprising 1,10-phenanthroline-2,9-dicarboxylic acid compounds selected from the group consisting of compounds of the formula (I)

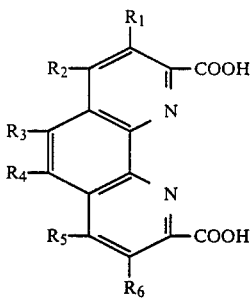 (I)

and trihalomethyl forms, salts, esters and acid halides thereof which are readily hydrolyzed to form the acid of the formula (I).

In the above formula $R_1$ to $R_6$ represent groups which may be substituted in the compound of formula (I) without deleteriously affecting the fluorescent activity of lanthanide chelates formed therefrom. In the preferred forms, the $R_1$ to $R_6$ substitients serve to enhance or advantageously modify the fluorescent activity of said chelates Each $R_1$ to $R_6$ may be independently hydrogen, $X-(R_7)_n-$ or $R_8-$, wherein X is $-SO_3-M^+$, wherein $M^+$ is a metal ion, a functional group which couples covalently with proteins or a group readily convertible to such functional group, $R_7$ is a divalent aliphatic residue having 1 to 12 carbons, or a divalent carbocyclic or heterocyclic residue having 3 to 12 carbons, and n is 0 or 1, and wherein $R_8$ is an aliphatic group having 1 to 12 carbons, or a carbocyclic or heterocyclic group having 3 to 12 carbons or one or more pairs of adjacent R1 to R6 groups form together with the carbons to which they are substituents (a) a carbocylic or heterocyclic ring containing 3 to 12 carbons, (b) an X-substituted carbocyclic or heterocyclic ring of the general formula (Ia):

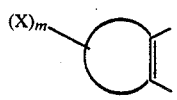 (Ia)

wherein ◯
is a divalent carbocyclic or heterocyclic residue having 1 to 12 carbons, X has the signification given above, and m is an integer from 1 to 4 or (c) an orthoquinone linkage:

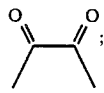;

with the proviso that: at least one of $R_1$ to $R_6$ is $X-R_7-_n$, wherein X, $R_7$ and n have the significations qiven above, or at least one pair of adjacent $R_1$ to $R_6$ groups form a ring of the formula (Ia) given above or an orthoquinone linkage As noted above $-R_7-$ and $R_8-$ may be the divalent residues and the monovalent residues, respectively, of an aliphatic compound, e.g. an alkane or alkene, having 1 to 12 carbons. Such aliphatic compound may be branched or straight chain.

When $R_7$ is a divalent carboxylic residue, $R_7$ may be a divalent residue of a simple (single ring) aromatic compound, e.g. phenylene, or the divalent residue of a condensed nuclear hydrocarbon e.g. of naphthalene, or of an alicyclic compound whether saturated, e.g. cyclohexane or unsaturated, e.g. cyclohexene, having 3 to 12 carbons.

Similarly, $R_8$ may be a simple aromatic group e.g. phenyl, or a condensed nuclear hydrocarbon group, e.g. naphthyl group, or a saturated or unsaturated alicyclic group e.g. cyclohexyl or cyclohexenyl.

$R_7$ may be a divalent residue of a simple heterocyclic compound, with or without unsaturation in the ring, e.g. $R_7$ may be a divalent residue of morpholine, or may be the divalent residue of a compound containing two or more condensed rings one or more of which may be heterocyclic ring, e.g. $R_7$ may be a divalent residue of quinoline or of purine.

Similarly $R_8$ may be a simple heterocyclic group e.g. morpholino or may be a group combining condensed rings e.g. quinolinyl.

Where an adjacent pair of $R_1$ to $R_6$ groups form a carboxylic or heterocyclic ring, with or without one or more X-substituents, such ring may be a simple ring or a condensed ring, e.g. one of the aromatic, alicyclic or heterocyclic ring systems mentioned above.

More specifically, one preferred class of compounds in accordance with the invention comprises 1,10-phenanthroline-2,9-dicarboxylic acid compounds selected from the qroup consisting of compounds of the formula

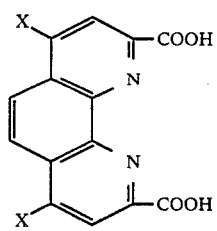 (II)

wherein each X is the same or different and is $-SO_3-M^+$, a functional group which couples covalently with proteins, a group readily convertible to such functional group, or is

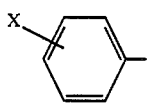 (IIa)

wherein X is a functional group which couples covalently with protein or a group readily convertible to such functional group, and trihalomethyl forms salts, esters and acid halides thereof which are readily hydrolyzed to form the acid of formula (II).

We have found that of the above group of compounds, derivatives of 4,7-diphenyl-1,10-phenanthroline-2,9-dicarboxylic acid (hereinafter DPPDA) are more suitable for fluorescent immunoassay because they absorb light in the 300–350 nm region which eliminates the need for quartz optics required for ligands having absorption maxima at lower wavelengths.

Thus a preferred class of compounds comprises 4,7diphenyl-1,10-phenanthroline-2,9-dicarboxylic acid compounds of the formula

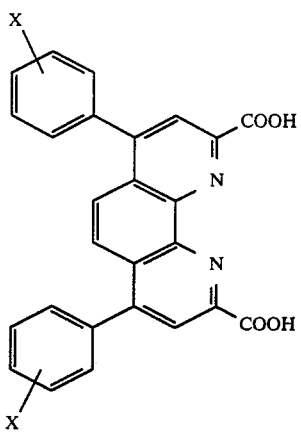

(III)

wherein each X is the same or different and is SO$_3$—M$^+$, a functional group which couples covalently with proteins, a group readily convertible to such functional group, and trihalomethyl forms, salts, esters and acid halides thereof which are readily hydrolyzed to form the acid of formula (III).

A further exemplary class of compounds in accordance with the invention comprises derivatives of 4,5,9,14-tetraaza-(1,2,3,4)-dibenzanthracene-3,6-dicarboxylic acid (hereinafter TADDA) of the formula

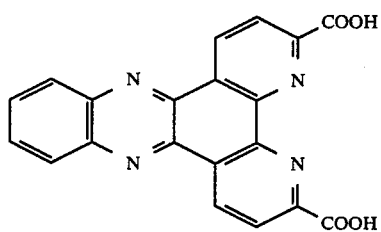

Compounds in accordance with the invention which are derivatives of TADDA have the formula

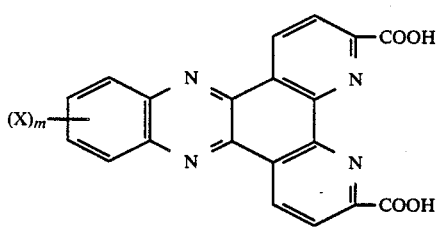

(V)

wherein X is SO$_3$—M$^+$, a functional group which couples covalently with proteins, a group readily convertible to such functional group, and m is an integer from 1 to 4.

As far as the inventors are aware, DPPDA, TADDA and their derivatives are novel compounds. DPPDA and TADDA are useful intermediates for preparation of markers for fluorescent assay of proteins since the phenyl rings and benzo substituent thereof provide convenient sites for derivatization by substitution therein of functional groups which couple covalently with proteins.

The marker compounds of the general formula (I) given above wherein a pair of adjacent R$_1$ to R$_6$ substituents form an orthoquinone linkage may be coupled to proteins through the known reaction mechanisms whereby orthoquinones react with amino compounds, to form protein-marker conjugates.

Examples of suitable functional groups (i.e. examples of X— in the above formulae) include diazonium, isothiocyanato and succinamic acid groups i.e. of the formulae

wherein Y is a monovalent anion, S=C=N— and

In the above diazonium groups, Y can be any anion which forms diazonium salts reactive with proteins. Examples of suitable anions include halide ions and acid sulphate ion, HO$_3$SO—. Preferably Y— is chloride.

While various examples of protein coupling groups X— have been given above, the invention is by no means limited to the use of the above-mentioned groups. For example, X— may be the monovalent residue of any compound which can be substituted in aromatic rings and which provides an atom or group capable of linking covalently with proteins, for example with lysine ε-amino groups or with N-terminal amino groups of proteins. Various such compounds are known in the prior art and need not be discussed in detail herein.

A particularly preferred class of compounds useful as markers for fluorescent immunoassay comprises those in which the functional coupling groups X— are halosulfonyl groups of the formula ZSO$_2$— wherein Z is halogen, and more preferably chlorine, obtained by reaction of a halosulfonic acid ZSO$_3$H with, for example DPPDA. Certain of the halosulfonyl compounds, and more particularly the halosulfonyl derivatives of DPPDA, form lanthanide chelates which provide remarkably high fluorescent intensities.

Further examples of the groups X— in the above formulae include hydroxyalkyleneaminosulfonyl groups e.g.

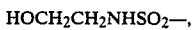

azo groups, e.g.

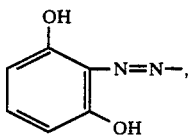

and hydroxyalkyleneaminothiocarbamyl groups, e.g.

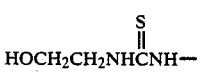

While such groups are not capable of coupling direct with proteins, they are readily convertible to groups capable of such coupling. For example, the hydroxyalkylene groups of the above hydroxyalkyleneaminosulfonyl and hydroxyalkyleneaminothiocarbamyl groups may be readily oxidized to, for example, aldehyde, using oxidative enzymes such as horse liver alcohol dehydrogenase (HLAD) in the presence of a hydrogen-accepting co-enzyme e.g. NAD, in accordance with the reaction scheme:

The aldehyde groups thus formed are capable of coupling with amino groups of proteins e.g. through the Schiff base forming mechanism.

The azo compound mentioned above has aromatic ring sites adjacent the —OH groups which are highly active and readily accept electrophilic substituents e.g. halosulfonation to yield halosulfonyl groups which can couple readily with proteins.

In the compounds having the functional groups X— substituted in the phenyl rings of DPPDA, each X may be the same or different and the X-substituent may be in the 2-, 3- or 4- positions. Conveniently, however, for ease of manufacture and of use of the markers, each X is the same and each is in the 4- position.

In the compounds having the functional group or groups X— substituted in the terminal benzo group of TADDA, each X may be the same or different and may be in the 10-, 11-, 12- or 13 positions. Conveniently, for ease of manufacture and use of the markers, each X is the same and the molecule contains an X— group in each of the 11- and 12- positions.

In the preferred forms of the present compounds, the or each group X— is free from nitrogen atom having an unshared pair of electrons adjacent the aromatic or heterocyclic ring to which the group X— is attached. We have found that the presence of such nitrogen atom in compounds of the general formula (I) significantly reduces the fluorescent intensities of the lanthanide chelates formed from the compounds.

Thus, for example, the fluorescent intensities of compounds of the formula (III) above having various X-substituents, in the presence of excess europium in aqueous solution, expressed in percentages relative to that of the unsubstituted compound DPPDA, are as follows:

TABLE 1

| X Groups | Relative Intensity |
|---|---|
| H—, (DPPDA) | 100 |
| NO$_2$—, | 41 |
| $\underset{\text{CH}_3-\overset{\text{O}}{\overset{\|}{\text{C}}}-\text{NH}-}{}$ | 5.2 |
| $\underset{\text{HOOCCH}_2\text{CH}_2\overset{\text{O}}{\overset{\|}{\text{C}}}-\text{NH}-}{}$ | 8.5 |
| NH$_2$—, | 0.27 |

Although applicants do not wish to be bound by any theory, it is suggested that the progressive impairment of the fluorescent intensities is evidenced in the above Table as a result of electron donation by the nitrogen atom to the marker molecule, so that there is an increase in its $\lambda_{max}$ of excitation and its excited state is no longer at an energy level effective to transfer energy to the europium or other lanthanide ion.

In contrast, the fluorescent intensities achieved with preferred compounds wherein the group X— does not have a nitrogen with unshared electrons adjacent the aromatic or heterocyclic rings, are much greater. For example, the preferred sulfonyl chloride derivative of DPPDA hydrolyzes in the presence of water to yield DPPDA disulfonate which in the presence of europium ions forms a chelate exhibiting fluorescent intensity 2% greater than that of the DPPDA chelate (X is H— in the above Table).

The soluble compounds wherein the group X is a sulfonate e.g. —SO$_3^-$M$^+$ wherein M$^+$ is a metal ion e.g. sodium, potassium, etc. are not capable of coupling with proteins. However it has been found that certain of these compounds and more notably 4,7-diphenyl-1,10-phenantholine-2,9-dicarboxylic acid disulfonate i.e. the compound of formula III wherein each X— is —SO$_3^-$M$^+$ produce high fluorescent intensities in the presence of europium but do not fluoresce in the presence of other lanthanides such as terbium (III), samarium (III) and dysprosium (III) salts. Thus these compounds may be employed as a water-soluble selective reagent capable of indicating or determining europium in the presence of other lanthanides.

With regard to the compounds wherein X is a group which couples covalently with proteins, such compounds may be used as markers for determining the concentration of an immunoreactive protein, e.g. an antigen, antibody or hapten in a sample of unknown concentration. The assay is performed by coupling the protein covalently to the marker compound, chelating the conjugate thus formed with a lanthanide salt, exposing the chelated conjugate to fluorescence stimulating radiation, determining the intensity of the fluorescence thereby stimulated, and deriving a value indicative of the concentration of the protein in the sample.

Preferably, in forming the protein-marker conjugates, the compounds of the above formulae (I), (II), (III) and (V) are used in the free diacid form. Where this is more convenient or desirable, it is however possible to supply the compounds in the form of trihalomethyl derivatives, e.g trichloromethyl wherein —COOH in the above formulae is replaced by —CCl$_3$, salts, for example sodium salts, esters, for example n-propyl diesters, or acid halides, for example chlorides, of the said diacids which are readily hydrolyzed to the free diacid form, it then being necessary merely to hydrolyze the said trihalomethyl form, salts, esters or acid halides to obtain the free diacid which forms a chelate with the lanthanide.

The lanthanide salt may be any which forms fluorescent chelates with the marker or conjugate. Examples include terbium and samarium salts and, more preferably, europium salts.

The assay may be conducted by comparing the fluorescent intensity of the chelated protein-marker compound conjugate with that of a sample containing a known concentration of the same chelated protein-marker conjugate, or, in some cases, by direct measurement of the fluorescent intensity of the sample containing an unknown concentration of the chelated protein-marker conjugate.

The protein-marker compound conjugate can be used in association with Lewis base synergists which enhance the fluorescence of the lanthanide chelate when water is present by removing water molecules from the coordination sphere of the metal ion. Such synergists may be tri-n-octylphosphineoxide (TOPO); dihexyl sulfoxide and tri-n-butyl phosphate. It is however, one advantage of the preferred markers of the invention that they form highly fluorescent chelates in aqueous solution, providing fluorescent intensities satisfactory for assay purposes, without requiring additions of such synergists.

The markers of the present invention form protein-marker conjugate chelates with long fluorescence decay times and therefore suitable for time-resolved fluorescene immunoassay. The preferred markers form conjugate chelates which exhibit such high fluorescent intensities that assays with good sensitivity and wide dynamics range can be conducted even with the use of a non-gated fluorometer.

As noted above, one preferred class of markers in accordance with the invention comprises derivatives of 1,10-phenanthroline-2,9-dicarboxylic acid (i.e. PDCA, the compound of formula (II) in which X is H). We have found that PDCA is a ligand which forms chelates with lanthanides, for example trivalent europium salts, which are highly fluorescent in aqueous solution without requiring the use of any Lewis base synergist. Without wishing to be bound by any theory, it is suggested that the phenanthroline diacid compounds function as tetradentate ligands with lanthanides such as europium, terbium and samarium.

As will be readily appreciated, markers useful for fluorescent immunoassay of proteins may be readily formed by derivatization of PDCA to introduce functional groups X—, for example the above-mentioned groups to obtain compounds of the formula (II) above which are capable of coupling covalently with protein molecules.

We have found that, whereas PDCA chelates have maximum excitation wavelengths below about 300 nm, chelates of DPPDA, TADDA and their derivatives exhibit maximum excitation wavelengths above about 300 nm, thus avoiding the need for quartz optics in the optical systems employed in the fluorescent immunoassay. Without wishing to be bound by any theory, it is suggested that the relatively short wavelengths of excitation of PDCA chelates is because phenanthrolines do not possess extensive conjugation of $\pi$-electrons, and the double bond between the 5,6-carbons is rather isolated. The introduction of phenyl groups into the phenanthroline ring system, as in DPPDA, or of a conjugated heterocyclic ring system, as in TADDA, appears to modify the electron conjugation system and increases the $\lambda$ max of excitation. The phenyl groups of DPPDA and the terminal benzene ring of TADDA further provide sites which may be readily derivatized by substitution of functional groups, for example the functional groups mentioned above, to form compounds of the formula (III) or (V) above which are capable of coupling covalently with protein molecules.

In the case of TADDA, for example, as will readily be appreciated by those skilled in the art, reactive functional groups such as isothiocyanato, diazonium or sulfonyl halide may be readily introduced at any one or more of the 10, 11, 12 or 13- positions.

Preparation of Ligands PDCA, DPPDA and TADDA 1,10-phenanthroline-2,9-dicarboxylic acid (PDCA) is a known compound and may be prepared by a two-step oxidation of 2,9-dimethyl-1,10-phenanthroline (neocuproine) with selenium dioxide followed by nitric acid, as described by Chandler et al, J. Heterocylic Chem., 18, 599–01 (1981).

We have found that 4,7-diphenyl-1,10-phenanthroline-2,9-dicarboxylic acid (DPPDA) may be prepared from 2,9-dimethyl-4,7-diphenyl-1,10-phenanthroline (bathocuproine) by oxidation with selenium dioxide to form 4,7-diphenyl-1,10-phenanthroline-2,9-dicarboxyaldehyde, followed by oxidation to the acid with nitric acid or by chlorination with N-chlorosuccinimide to form 2,9-bis(trichloromethyl)-4,7-diphenyl-1,10-phenanthroline, and subsequent hydrolysis, in accordance with the following reaction schemes:

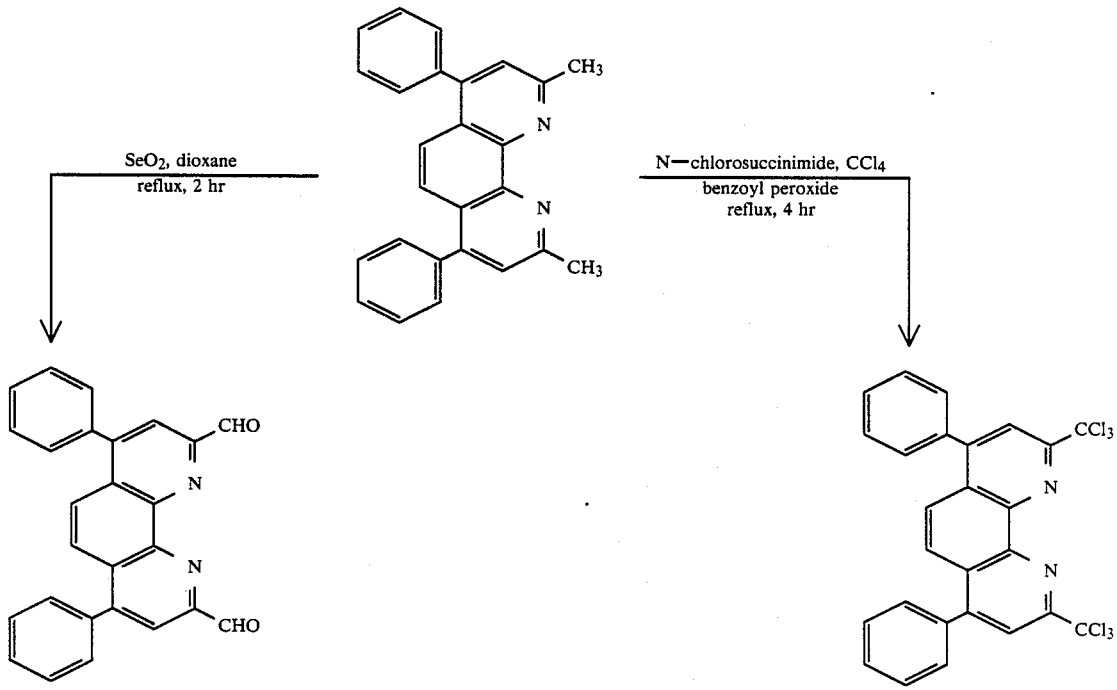

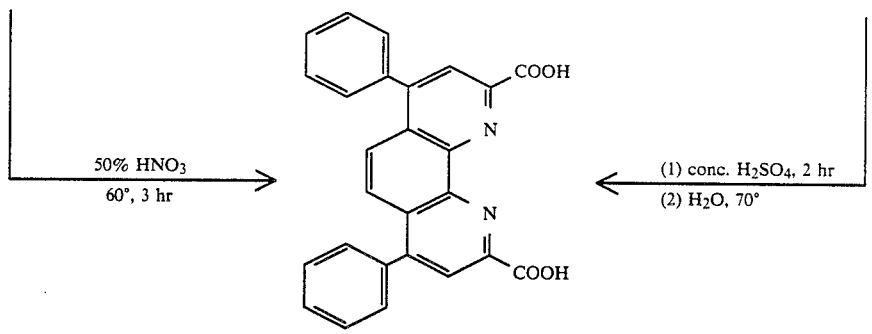

TADDA may prepared for neocuproine by forming a cobalt coordination complex of neocuproine to facilitate the oxidation of the 5, 6-carbon carbon double bond to the 5,6 quinone, which oxidation may be performed using potassiuim bromide, sulfuric acid and nitric acid, followed by demetallation of the quinone with ethylenediaminetetraacetic acid, condensation of the quinone with o-phenylenediamine to form the dimethyl analog of the desired dicarboxylic compound, and chlorination of the methyl groups and hydrolysis to form the dicarboxylic acid, in accordance with the following reaction scheme:

Some non-limiting examples of methods of preparation of ligands will now be given.

EXAMPLE 1-SYNTHESIS OF DPPDA

Example 1a

Synthesis of 4,7-diphenyl-1,10-phenanthroline-2,9-dicarboxaldehyde

A mixture of bathocuproine (0.8 g, 2.2 mmole), selenium dioxide (1.16 g, 10.4 mmole), dioxane (29.6 ml) and water (1.25 ml) was heated with stirring in an oil bath at 110° for 2 hr. The hot mixture was then filtered through Celite to remove selenium metal. Water was

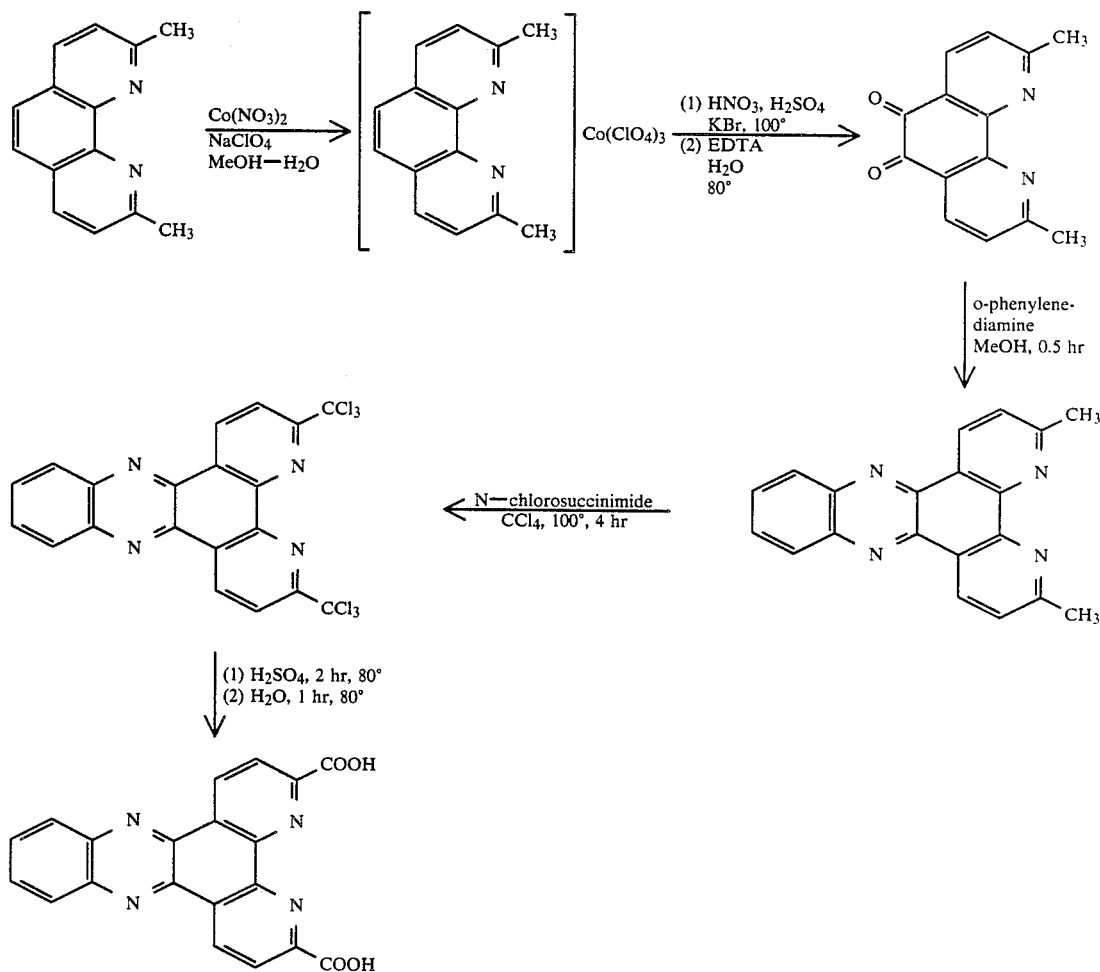

added to the hot filtrate until slight cloudiness appeared. The mixture was then placed in the refrigerator to allow the product to precipitate. The product, which was contaminated by red selenium metal, was collected by vacuum filtration. Yield=88%. Mp=165°–170°. IR 3200-3600, 2800-3050, 1717, 1590, 1550, 1495, 1445, 1400, 1355, 1295, 1255, 1190, 1120, 1080, 875, 780, 705, 620 cm$^{-1}$. 60 MHz proton NMR in CDCl$_3$ δ7.2 (10 protons), δ7.7, δ7.95 (4 protons), δ10.05 (<2 protons).

Example 1b

Synthesis of DPPDA from 4,7-diphenyl-1,10-phenanthroline-2,9-dicarboxaldehyde

A mixture of 4,7-diphenyl-1,10-phenanthroline-2,9-dicarboxaldehyde (0.76 g, 1.96 mmole), obtained as in Example 1a, in 9.2 ml 50% nitric acid was stirred for 3 hr in an oil bath at 60°. After cooling to room temperature, the mixture was poured into 50 ml of ice water. The product was collected by vacuum filtration, washed with water and dried in a vacuum dessicator. The product was recrystallized from hot methanol. Yield=80%. Mp=194°–198°. IR 2800-360, 2500 (shoulder), 1725, 1620, 1595, 1550, 1495, 1450, 1400, 1360, 1210-1310, 1130, 775, 705, 620 cm$^{-1}$. 60 MHz proton NMR in DMSO-d$_6$: δ7.6 (10 protons), δ8.0 (2 protons), δ8.3 (2 protons), δ6.5 (H$_2$O). Elemental analysis: found, 72.52%C, 3.66% H, 6.41% N; calculated for C$_{26}$H$_{16}$N$_2$O$_4$, 74.28% C, 3.84% H, 6.66% N.

EXAMPLE 2

Synthesis of DPPDA Example 2a

Synthesis of 2,9-bis(trichloromethyl)-4,7-diphenyl-1,10-phenanthroline

A mixture composed of 2,9,-dimethyl-4,7-diphenyl-1,10-phenanthroline (4.0 g, 0.011 mole), N-chlorosuccinimide (9.0 g, 0.067 mole), benzoyl peroxide (0.011 g) and 96 ml carbon tetrachloride was stirred for 6 hr in an oil bath at 90°. After standing overnight at 4° C., crystals of succinimide were removed by filtration. The solvent was removed from the filtrate by vacuum evaporation to produce a light yellow solid which was then dissolved in chloroform. The organic layer was washed with saturated sodium carbonate solution and dried over anhydrous magnesium sulfate. Removal of solvent by vacuum evaporation yielded the white solid product. Yield=6.1 g (97%). Mp=286°–289°. IR 3020-3080, 1620, 1570, 1550, 1490, 1445, 1405, 1360, 1220, 1040, 930, 895, 835, 800, 780, 760, 735, 700, 620 cm$^{-1}$. 60 MHz proton NMR in CDCl$_3$ δ7.55 singlet (10 protons), δ8.05 singlet (2 protons), δ8.3 singlet (2 protons).

Example 2b

Synthesis of DPPDA from 2,9-bis(trichloromethyl)-4,7-diphenyl-1,10-phenanthroline A mixture composed of 2,9-bis(trichloromethyl)-4,7-diphenyl-1,10-phenanthroline (6 g, 0.0106 mole), obtained as in Example 2a, in 15 ml concentrated H$_2$SO$_4$, was stirred in a 90° oil bath for 2 hr. After cooling to room temperature, 36 ml of water was added dropwise to the continuously stirred reaction mixture. The resulting suspension was heated in the 90° oil bath for 1 hr. The reaction mixture was cooled to room temperature and added to 150 ml ice water. The yellow solid product was collected by vacuum filtration. Yield=5.71 g (128%). The product was most probably wet or hydrated. Mp=180°–184° (unrecrystallized). IR 2800-3600, 2500 (shoulder), 1725, 1620, 1600, 1550, 1495, 1450, 1400, 1360, 1210-1310, 770, 705 cm$^{-1}$. 60 MHz proton NMR in DMSO-d$_6$: δ7.7 singlet (10 protons), δ8.0 singlet (2 protons), δ8,3 singlet (2 protons), δ6.3 (water).

EXAMPLE 3

Synthesis of TADDA

Example 3a

Preparation of tris (2,9-dimethyl-1,10-phenanthroline) cobalt (III) perchlorate

Neocuproine (1.00 g, 0.00480 mole) and cobalt (II) nitrate hexahydrate (0.466 g, 0.00160 mole) were dissolved in 30 ml 2:1 water-methanol with stirring in a 60° water bath. Sodium perchlorate solution (3.5 ml 1.5M) was added rapidly with stirring. A flaky pink precipitate was formed immediately. After cooling at 4° C., the product was collected by vacuum filtration and dried in vacuum. Yield=86%. IR: 2800-3700, 1630, 1600, 1570, 1500, 1425, 1390, 1360, 1300, 1030-1150, 860, 730, 625 cm$^{-1}$.

Example 3b

Preparation of 2,9-Dimethyl-1,10-phenanthroline-5,6-quinone hydrate

A mixture composed of 3.20 g (0.00326 mole) tris (2,9-dimethyl-1,10-phenanthroline) cobalt (III) perchlorate prepared as in Example 3a, 1.70 g (0.0143 mole) potassium bromide, 25 ml 96% sulfuric acid, and 14.5 ml 75% nitric acid was heated with stirring in a 100° oil bath for 1 hr. Bromine was liberated during the reaction. The mixture was cooled and added to 50 ml 3M sodium perchlorate solution to precipitate the cobalt-quinone complex. After overnight standing at 4° C., the yellow solid product was collected by vacuum filtration and washed with cold water.

The cobalt-quinone complex was added to a solution containing 2.5 g (0.0067 mole) of disodium ethylenediaminetetraacetic acid with pH adjusted to 5. The reaction mixture was heated with stirring at 80° for 1 hr. After cooling to 4° C., a yellow precipitate was collected by vacuum filtration. The product was contaminated by colourless crystals of what appeared to be an inorganic compound. The product was suspended in hot methanol and the insoluble solid was filtered off. The yellow solid product precipitated from the cooled methanol solution. More product was obtained by adding water to the methanol mother liquor. The yield from tris (2,9-dimethyl-1,10-phenanthroline) cobalt (III) perchlorate was 12%. IR: 2800-3700, 1690, 1580, 1435, 1380, 1310, 1090, 1030, 840, 625 cm$^{-1}$. 60-MH$_z$proton NMR in CDCl$_3$: 2.9 singlet (6 protons), 7.1-7.6 multiplet (2 protons), 8.0-8.6 multiplet (2 protons).

Example 3c

Preparation of 3,6-Dimethyl-4,5,9,14-tetraaza-(1,2,3,4)-dibenzanthracene 2,9-Dimethyl-1,10-phenanthroline-5,6-quinone hydrate, prepared as in Example 3b, (0.15 g, 0.00059 mole) was dissolved with stirring in 5 ml methanol at 60°. To this solution was added dropwise a solution of o-phenylenediamine (0.063 g, 0.00059 mole) in 1 ml methanol. A yellow precipitate was formed. The reaction was allowed to proceed with stirring for 30 min. After cooling, the solvent was removed completely by vacuum evaporation. The product was recrystallized from hot methanol. A solid which did not dissolve in hot methanol was removed by filtration. The solid which precipitated upon cooling the methanol solution to 4° C. contained two compounds as seen by silica gel thin-layer chromatography. The product was purified on 0.5 mm-thick preparative thin-layer silica gel plates with a green fluorescent indicator using ethyl acetate as eluting solvent. The product migrated to a shorter distance than the impurity. The silica gel was scraped from the plate and placed in a small column. The product was eluted with methanol. Pure product was obtained after evaporation of the solvent. The yield based on 2,9-dimethyl-1,10-phenanthroline-5,6-quinone hydrate was 22%. Mp=252°–255°. IR: 2800–3600, 1575, 1475, 1425, 1370, 1130, 1100, 1050, 830, 760, 740 cm$^{-1}$. 60-MH$_z$ proton NMR in CDCl$_3$: 2.95 singlet (6 protons), 7.15–8.20 multiplet (6 protons), 9.1–9.5 multiplet (2 protons).

Example 3d

Preparation of 3,6-Bis(trichloromethyl)-4,5,9,14-tetraaza-(1,2,3,4)-dibenzanthracene A mixture composed of 45 g (0.000145 mole) 3,6-dimethyl-4,5,9,14-tetraaza (1,2,3,4)-dibenzanthracene, 0.117 g (0.000876 mole) N-chlorosuccinimide, and 1.5 mg benzoyl peroxide in 3 ml carbon tetrachloride was heated with stirring in a 100° oil bath. After cooling, the insoluble succinimide was filtered off. The solvent was evaporated and the residue was dissolved in 20 ml chloroform. The chloroform solution was washed with saturated sodium carbonate solution and dried over anhydrous magnesium sulfate. The light yellow solid product was obtained by vacuum evaporation of the solvent. Yield=42%. IR: 2700–3100, 1570, 1485, 1375, 1360, 1220, 1095, 1050, 825, 790, 740 cm$^{-1}$. 60-MH$_z$ proton NMR in CDCl$_3$: 7.1–8.5 multiplet (6 protons), 9.4–9.7 doublet (2 protons).

Example 3e

Preparation of 4,5,9,14-Tetraaza-(1,2,3,4) dibenzanthracene-3,6-dicarboxylic acid (TADDA)

A mixture of 3,6-bis(trichloromethyl)-4,5,9,14-tetraaza-(1,2,3,4)-dibenzanthracene (32 mg, 6.2×10$^{-5}$ mole) and 0.5 ml 96% sulfuric acid was stirred for 2 hr in a 80° oil bath. After cooling, 1.2 ml water was added and stirring at 80° was continued for 1 hr. The reaction mixture was added to about 20 ml cold water to precipitate the product. Yield=87%. IR: 2700–3600, 2500 (shoulder), 1725, 1570, 1480, 1450, 1380, 1340, 1240, 1130, 1050, 785, 760, 720 cm$^{-1}$. UV spectrum in 1:1 methanol - DMF: 233 nm (log $\epsilon$=3.64), 277 nm (log $\epsilon$=4.62), 301 nm (log $\epsilon$=4.31), 354 nm (log $\epsilon$=3.86), 364 nm (log $\epsilon$=3.96), 383 nm (log $\epsilon$=3.96).

Fluorescence of PDCA, DPPDA and TADDA lanthanide chelates

PDCA-lanthanide solutions

Aqueous solutions were prepared containing various concentrations of europium chloride (ranging from 1×10$^{-10}$ to 1×10$^{-6}$ mole/l EuCl$_3$) in an excess of PDCA (5×10$^{-5}$M PDCA) in 0.05 TRIS (tris(hydroxymethyl)aminoethane) at pH 7.0. The fluorescence of these solutions was determined using a Perkin-Elmer fluorometer (non-gated). The fluorescence count ranged from about 0.204 for the lowest concentrations of EuCl$_3$ and up to about 288 for the highest concentrations. Similarly, the fluorescence of PDCA in an excess of EUCl$_3$, using aqueous solutions containing concentrations of PDCA ranging from 1×10$^{-10}$ to 1×10$^{-6}$ mole/l in 1×10$^{-5}$ EuCl$_3$) in 0.05M TRIS at pH 7.0 was determined and the fluorescence count was found to be about 0.088 for the lowest concentration of PDCA and about 15.9 for the highest. Thus, the PDCA-Eu system was found to be highly fluorescent in aqueous solution without the use of TOPO or other Lewis base synergist. Maximum excitation and emission occurred at 290 nm and 613 nm respectively. The limit of detection of europium in excess PDCA and of PDCA in the presence of excess europium each appeared to be 1×10$^{-10}$M.

DPPDA-lanthanide solutions

Using the method described above, aqueous solutions of DPPDA-Eu were found to be fluorescent in the absence of TOPO or other synergist with excitation and emission maxima at 330 nm and 613 nm, respectively. Aqueous solutions containing 1×10$^{-12}$ to 1×10$^{-6}$ mole/l EuCl$_3$ in an excess (1×10$^{-5}$M) of DPPDA, 0.1% SDS (sodium dodecyl sulfate) and 0.05M TRIS, at pH 8.5 yielded fluorescence counts of from about 1.36 to about 338, while solutions containing 1×10$^{-10}$ to 1×10$^{-6}$ mole/l DPPDA in excess (1×10$^{-5}$M) EuCl$_3$, in 0.05M TRIS at pH 8.5 yielded counts of 0.073 to 47.3. The limit of detection of DPPDA in the presence of excess EuCl$_3$ appeared to be 1×10$^{-10}$ mole/l.

TADDA—lanthanide solutions

A solution containing 1×10$^{-6}$M TADDA and 1×10$^{-5}$M EuCl$_3$ in 0.05M carbonate buffer pH 10 was found to be fluorescent with excitation maxima at 364 nm and 383 nm and emission maximum at 619 nm. The fluorescence in acetate buffer pH 5 and CAPS buffer pH 10 is about one-fourth the fluorescence intensity in carbonate pH 10. The fluorescence of the Eu-TADDA solution is only 2.2% that of the Eu-DPPDA solution carbonate buffer pH 10. It is suggested that the nitrogen atoms containing unshared pairs of electrons, in the 9,14-positions of the TADDA molecule, cause a decrease of fluorescence intensity as compared with that of Eu-DPPDA solutions.

Preparation of Preferred Marker and other Compounds

The intermediate compound 2,9-dimethyl-1,10-phenanthroline-5,6-quinone prepared in accordance with the reaction scheme given earlier may be chlorinated to form 2,9-bis(trichloromethyl)-1,10-phenanthroline-5,6-quinone which constitutes a useful precursor which is hydrolyzable to the final marker compound or dicarboxylic acid form, 1,10-phenanthroline-5,6-quinone-2,9-dicarboxylic acid, in accordance with the reaction scheme

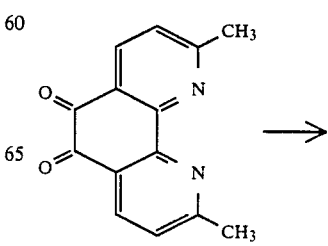

17
-continued

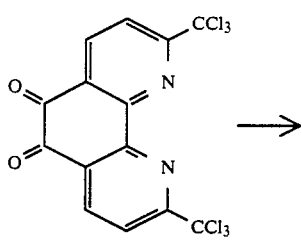

→

18
-continued

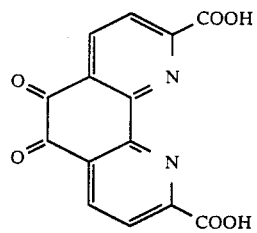

The bis-diazonium and bis-isothiocyanato derivatives of DPPDA can be prepared through nitration of DPPDA to form dinitro DPPDA, hydrogenation of the dinitro DPPDA to diamino DPPDA and then diazotization of the diamino DPPDA with nitrous acid or reaction with thiophosgene to form the diazonium compound or the isothiocyanato compound, in accordance with the following reaction scheme:

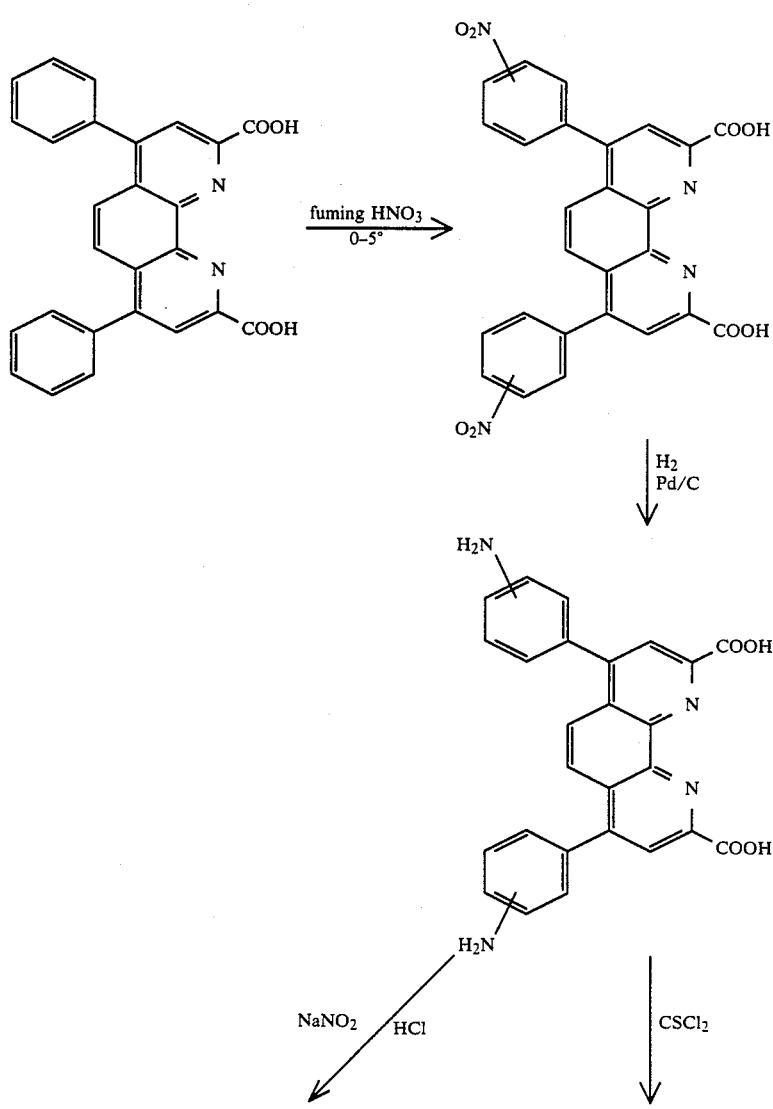

-continued

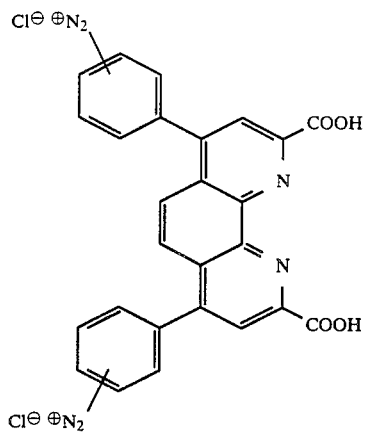 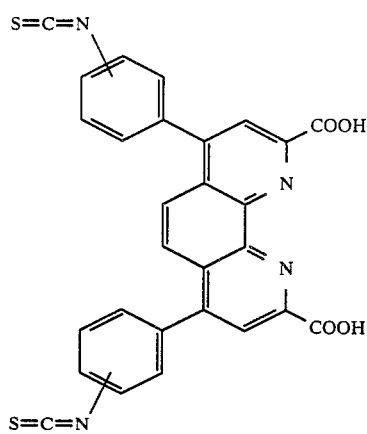

The bis(succinamic acid) derivative of DPPDA can be prepared by reaction of diamino DPPDA with succinic anhyydride, in accordance with the following reaction scheme:

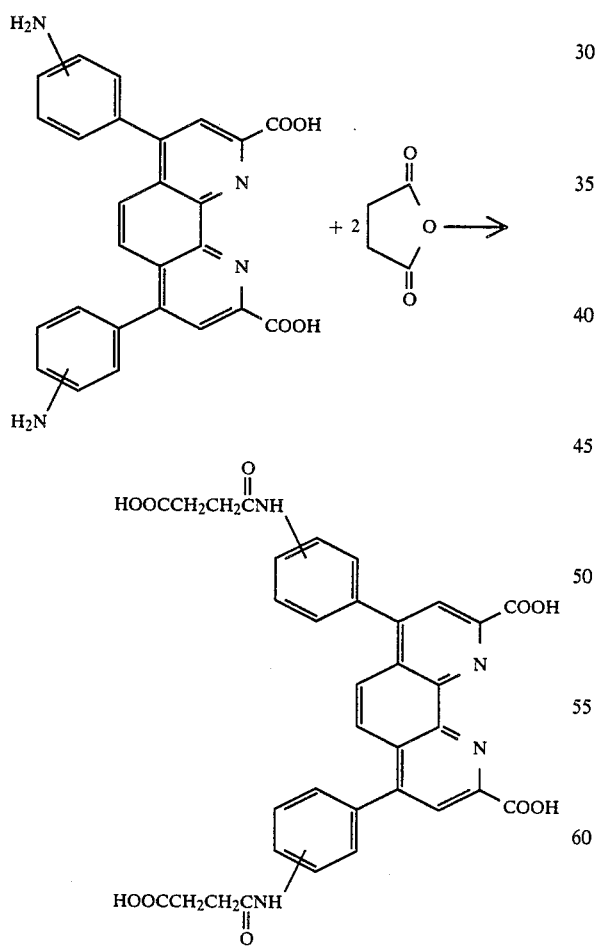

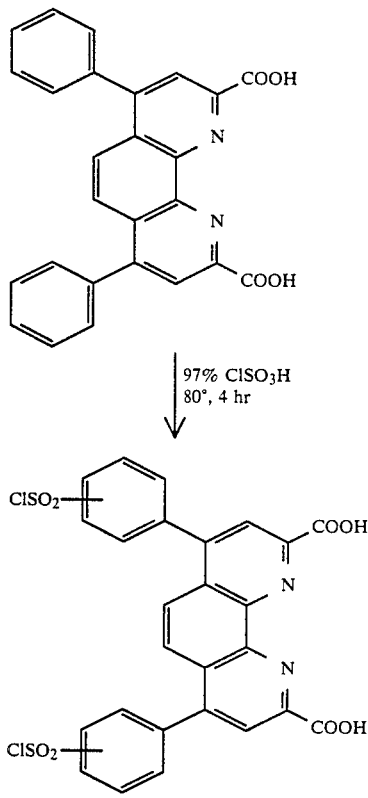

The bis(chlorosulfonylphenyl) derivative of DPPDA can be prepared by direct chlorosulfonation of DPPDA in accordance with the following reaction scheme:

Some non-limiting Examples of methods of preparation of preferred marker and other compounds will now be given.

EXAMPLE 4

Synthesis of 2,9-bis(trichloromethyl)-1,10-phenanthroline-5,6-quinone 2,9-dimethyl-1,10-phenanthroline-5,6-quinone hydrate, prepared as in Example 3b, was chlorinated according to the chlorination procedure described in Newkome et al, J. Org. Chem. 48, 5112 (1983) for 2,9-dimethyl-1,10-phenanthroline, using double the amount of solvent and sodium bicarbonate instead of sodium carbonate for washing the organic layer. The orange product of the title hereto was obtained without further purification in a yield of 54%. IR 1690, 1580, 1380, 1310, 1090, 790, 730 cm$^{-1}$.

EXAMPLE 5

Synthesis of 1,10-phenanthroline-5,56-quinone-2,9-dicarboxylic acid dihydrate A mixture composed of 0.69 g (1.55 mmole) of the quinone of Example 4 and 3 ml concentrated sulfuric acid was heated with stirring over an oil bath at 80° for 1 hour. The cooled reaction mixture was added to 40 ml ice water to precipitate the product. The yellow solid product was collected by vacuum filtration and dried in vacuum. The product was recrystallized twice from methanol-water. The yield was 52 mg (11%). Mp>300°. IR 2800–3600, 2500 (shoulder), 1720, 1700, 1620, 1570, 1430, 1380, 1220–1300, 1020, 930, 870, 800, 720 cm$^{-1}$. $^1$H nmr in DMSO-d$_6$δ: 8.3(d,2H), 8.7(d,2H). Anal. calcd for C$_{14}$H$_{10}$N$_2$O$_8$): C 50.31, H 3.02, N 8.38; found: C 49.99, H 2.35, N. 8.64.

EXAMPLE 6

Synthesis of 4,7-bis(nitrophenyl)-1,10-phenanthroline-2,9-dicarboxylic acid (dinitro DPPDA)

Solid DPPDA (0.42 g, 1 mmole) of Example 1b was added in small portions to 3 ml of cold 90% HNO$_3$. The mixture was stirred for 4.5 hr in an ice bath. The reaction mixture was then poured into 100 ml crushed ice to produce a yellow solid. The product was collected by vacuum filtration and dried in a vacuum oven at 60° C. Yield=96% IR 2800–3650, 2500 (shoulder) 1725, 1605, 1520, 1445, 1395, 1350, 1200–1310, 860, 850, 770, 730, 705 cm$^{-1}$.

EXAMPLE 7

Synthesis of 4,7-bis(aminophenyl)-1,10-phenanthroline-2,9-dicarboxylic acid disodium salt (diamino DPPDA)

Dinitro DPPDA (0.44 g, 0.85 mmole) of Example 4 was hydrogenated at atmospheric pressure in 400 ml 1:1 methanol-water 0.001M NaOH solution pH 11 with vigorous stirring over 0.5 g 10% palladium-on-charcoal catalyst. After 6.5 hr, 0.15 g fresh catalyst was added and hydrogenation was continued for another 1.5 hr. The product was obtained after removal of the catalyst by vacuum filtration through a fine filter paper and vacuum evaporation of the solvent. Yield=47% IR 2800–3700, 1610, 1350–1500, 1150, 880, 840, 810 cm$^{-1}$.

EXAMPLE 8

Synthesis of DPPDA bis (succinamic acid)

The diamino DPPDA disodium salt (0.20 mmole) of Example 7, 61 mg of succinic anhydride (0.61 mmole), 85 l of triethylamine (0.61 mmole) and 10 mg of 4-dimethylaminopyridine were stirred in 10 ml dry DMF (N,N-dimethylformamide) for 4 hr at room temperature. The solvent was removed by vacuum evaporation (0.1 mm Hg). Ten milliliters of 10% NaHCO$_3$ was added to the residue. The mixture was filtered and the filtrate was acidified to pH 2 with dilute HCl. Evaporation of the acidified filtrate yielded succinic acid. The solid which did not dissolve in 10% NaHCO$_3$ was suspended in hot methanol. After filtration and evaporation of methanol, a greenish-brown solid was obtained. The solid was suspended in dilute HCl, isolated by centrifugation and dried in vacuum.

Yield=30 mg (23%).

IR 2800–3600, 2500 (shoulder), 1720, 1390–1650, 1100–1450, 840, 800, 740, 700 cm$^{-1}$.

EXAMPLE 9

Synthesis of 4,7-bis(acetamidophenyl)-1,10-phenanthroline-2,9-dicarboxylic acid A mixture of 45 mg (0.091 mmole) of the bis(aminophenyl) compound, prepared as described in Example 7, 6 ml (64 mmole) acetic anhydride and 0.4 ml (0.49 mmole) pyridine was heated in a 100° oil bath for 4 hr. The volatiles were removed by vacuum evaporation and the residue was suspended in water. The pH was adjusted to 3 and the product was collected by vacuum filtration. The yield was 62%. IR 3200–3600, 3000, 1710, 1640, 1570, 1410, 1040, 1010, 920, 805, 645 cm$^{-1}$.

EXAMPLE 10

Synthesis of 4,7-bis(diazophenyl)-1,10-phenanthroline-2,9-dicarboxylic acid-resorcinol adduct An aqueous solution of sodium nitrite (0.25 ml of 0.5M solution) was added dropwise to a stirred solution of the bis(aminophenyl) compound prepared as in Example 7, (24 mg, 0.050 mmole), 0.25 ml water, and 0.50 ml concentrated hydrochloric acid in an ice bath. The diazotization was allowed to proceed with stirring for 1 hr at 0°. Solid urea (3 mg, 0.050 mmole) was added to destroy the excess NaNO$_2$. The reaction mixture was diluted to 10 ml with cold water to form a 5 mM diazonium salt stock solution.

For the diazo coupling reaction, 0.5 ml of the 5 mM diazonium salt solution was neutralized with solid NaHCO$_3$ to pH 8. The resulting solution was added to a cold aqueous resorcinol solution (0.5 ml of 0.01M) and the coupling was allowed to proceed for 1 hr with stirring at 4°. The mixture was acidified to pH 2 by addition of dilute hydrochloric acid. The red solid product was collected by centrifugation, washed with water and dried in a vacuum oven at 60°. The yield was 16 mg (92% based on the diazo compound, assuming quantitative diazotization). IR 2800–3600, 2500 (shoulder), 1720, 1610, 1475, 1405, 1320, 1230, 1120, 840, 790 cm$^{-1}$.

EXAMPLE 11

Synthesis of 4,7-bis(isothiocyanatophenyl)-1,10-phenanthroline-2,9-dicarboxylic acid 0.15 g (0.30 mmole) of the bis(aminophenyl) compound prepared as in Example 7 was dissolved in 10 ml water. The pH was adjusted to 7 by addition of dilute hydrochloric acid. Thiophosgene (Aldrich) (0.16 ml, 2.0 mmole) was added and the mixture was shaken for 1 hr at room temperature in a fume hood. Excess thiophosgene was removed by extraction with ether. The pH of the aqueous layer was adjusted to 1 and water was removed in vacuum to yield 30 mg (18% yield) of the title compound. IR 2800–3600, 2500 (shoulder), 2060, 1725, 1495, 1445, 1400, 1250, 1130, 930, 840, 770, 749 cm$^{-1}$.

EXAMPLE 12

Synthesis of 4,7-bis(2-hydroxyethylaminothiocarbamylphenyl)-1,10-phenanthroline-2,9-dicarboxylic acid A solution of the bis(isothiocyanatophenyl) compound, prepared as in Example 11, (20 mg, 0.038 mmole) in 0.5 ml DMF was added to a stirred solution of ethanolamine (85 μl, 1.4 mmole) in 3 ml 0.1M carbonate buffer pH 10. The thiourea formation was allowed to proceed with stirring for 2 hr at room temperature. The pH was then adjusted to 3 by addition of dilute hydrochloric acid to precipitate the product. The product was collected by vacuum filtration, washed with water and dried in vacuum. The yield was 23 mg (94%). IR 2800–3500, 2500 (shoulder), 1720, 1660, 1600, 1540, 1445, 1405, 1320, 1245, 1060, 840 cm$^{-1}$.

EXAMPLE 13

Synthesis of 4,7-bis(chlorosulfonylphenyl)-1,10-phenanthroline-2,9-dicarboxylic acid (bis(chlorosulfonyl)DPPDA)

DPPDA (2 g, 0.0048 mole) of Example 2b was added in small portions to 10 ml of continuously stirred cold 97% chlorosulfonic acid. The resulting mixture was stirred for 4 hr in a 80° oil bath. After cooling to room temperature the mixture was added cautiously to 200 ml stirred ice water which was cooled externally by a large ice bath. The light yellow product precipitated immediately. The product was collected on a sintered glass funnel by vacuum filtration and dried in vacuum (0.1 mm Hg) for 12 hr. The product was stored under argon in a dessicated jar at −20° C. Yield=2.28 g (78%). Mp>300°. IR 2800–3600, 2500 (shoulder), 1730, 1620, 1595, 1510, 1480, 1450, 1380, 1310, 1220, 1180, 1030, 895, 840, 780, 740, 695, 620 cm$^{-1}$. 60 MHz NMR in DMSO-d$_6$: 7.9 doublet (8 protons), 8.1 singlet (2 protons), 8.5 singlet (2 protons). Elemental analysis: found 49.82%C, 2.18%H, 4.16%N, 9.26%A; calculated for $C_{26}H_{14}N_2Cl_2S_2O_8$, 50.58%C, 2.28%H, 4.54%N, 11.48%Cl.

EXAMPLE 14

Synthesis of 4,7-bis(2-hydroxyethylaminosulfonylphenyl)-1,10-phenanthroline-2,9-dicarboxylic acid The bis(chlorosulfonyl) compound, prepared as in Example 13, (61.7 mg, 0.1 mmole) in 0.5 ml dry DMF was added dropwise to a stirred solution of 0.12 ml (2 mmole) ethanolamine (Fisher) in 7 ml 0.1M carbonate buffer pH 10. The sulfonyl chloride precipitated but dissolved completely after 2 min. The sulfonamide formation was allowed to proceed with stirring for 2 hr at room temperature. The mixture was then acidified to pH 2 by addition of dilute hydrochloric acid to precipitate the product. The mixture was cooled to 4° C. and the product was collected by centrifugation. The product was washed with water and dried in a vacuum oven. The yield was 68% based on 15. Mp>300°. IR 2800–3600, 2500 (shoulder), 1725, 1620, 1410, 1320, 1155, 1100, 775 cm$^{-1}$.

EXAMPLE 15

Synthesis of 4,7-diphenyl-1,10-phenanthroline-2,9-dicarboxylic acid disulfonate

Solid bis(chlorosulfonylphenyl) compound, prepared as described in Example 13, (6.17 mg, 0.01 mmole) was added to 10 ml 0.05M carbonate buffer pH 10. The mixture was heated with stirring at 60° for 1 hr. The sulfonyl chloride dissolved gradually as it hydrolyzed to form a 1 mM solution of the disulfonate compound of the title (sodium form).

Formation of protein-marker conjugates

The preferred markers of the invention react through various mechanisms to couple covalently with immunoreactive or other proteins. For example, markers having as the functional group X—a diazonium group $Y-_2-N^+$—can couple covalently with aromatic amino acid residues such as tyrosine and histidine residues present in the protein, and isothiocyanato groups readily couple covalently with amino groups present in proteins to form thioureas.

Marker compounds having succinamic acid groups can couple covalently with protein amino groups through carbodiimide coupling. Since the carboxylic acid groups at the 2,9-positions in the phenanthroline ring system may also react with amino groups present in proteins, it is desirable to conduct the coupling reactions in the presence of an agent which protects these carboxylic acid groups, for example a metal cation with which the acid groups from a chelate, such as europium or other lanthanide ion.

The marker compound having sulfonyl halide groups are reactive toward lysine ε-amino groups and N-terminal amino groups of proteins and covalent coupling of the marker occurs through sulfonamide formation. The best yields of labelled protein are achieved by adding the marker compound in a polar solvent, e.g. DMF, to a continuously stirred solution of the protein in an alkaline buffer solution, e.g. carbonate or borate buffer solution at pH 9.

Some non-limiting Examples of coupling of preferred marker compounds with proteins to form protein-marker conjugates will now be given.

EXAMPLE 16

Attachment of DPPDA bis (succinamic acid) to bovine serum albumin

Two milligrams of DPPDA bis (succinamic acid) (3.1 mmole) of Example 6 was suspended with stirring in 2.5 ml 0.1M phosphate buffer pH 4.8. Thirty microliters of 0.01M EuCl$_3$ solution (0.3 mmole) and 2 mg BSA bovine serum albumin (BSA) (0.03 mmole) were added. A solution containing 1.7 mg (0.1 mmole) 1-(3-dimethylaminopropyl)-3-ethylcarbodiimide hydrochloride (EDC - a water-soluble condensing agent for formation of amides from carboxylic acids and amines) in 0.5 ml water was added to the mixture with stirring. The conjugation was allowed to proceed with stirring for 4 hr at room temperature. The solution was then dialyzed against 0.05M TRIS buffer pH 7.5. The dialysis solution was changed four times. The conjuqate solution was diluted to 25 ml to produce 80 μg/ml labelled protein which was stored at 4° C. with 0.02% sodium azide.

When examined for fluorescence with a Perkin-Elmer fluorometer (non-gated), solutions of the DPPDA bis (succinamic acid)-labelled BSA exhibited fluorescence in the presence of excess europium with excitation maximum at 340 nm and emission maximum at 617 nm. Solutions of the labelled BSA ranging in concentration from about 2 ng/ml up to $10^4$ ng/ml in $1\times10^{-5}$M EuCl$_3$ solution, 0.05M TRIS pH 8.5, yielded fluorescence counts of from about 0.023 for the lowest concentration up to about 20.1 for the highest. The results indicated that a minimum concentration of about 1 ng/ml labelled protein could be detected using a non-gated fluorometer.

EXAMPLE 17

Protein labelling with DPPDA bis(chlorosulfonyl)

In a typical labelling experiment, 1 or 2 mg of an antigen or antibody (BSA, mouse IgG, goat anti-mouse IgG, or goat anti-human IgG) was dissolved in 2 ml carbonate buffer pH 9. DPPDA bis(chlorosulfonyl) (0.4 or 0.8 mg, 100 equivalents) was dissolved in 0.2 ml DMF which was dried over molecular sieves 4A and distilled. The resulting DMF solution was added dropwise to the continuously stirred antigen or antibody solution over a period of 5 min. The mixture was then stirred for 4 hr at room temperature in the dark to allow coupling to occur. Unbound excess reagent was removed by dialysis against four 800 ml portions of 0.05M TRIS pH 7.5. In cases where a small amount of insoluble material was formed, the mixture was cenrifuged at 1500 rpm for 15 min and the precipitate was removed. The labelled antigen or antibody solution was stored at a concentration of 40 or 50 µg/ml in 0.05M TRIS pH 7.5 containing 0.05% NaN$_3$.

A Bio-Rad protein assay of the labelled protein solution using human IgG as standard showed that 70–100% of the proteins were usually recovered after labelling and dialysis. The Bio-Rad protein assay reagent contains Coomassie Brilliant Blue G-250 which undergoes a shift in visible light absorption upon binding to proteins. The labelled antibody solutions were most fluorescent in the presence of europium in the pH range 9–10 in carbonate, borate, or 3-cyclohexylamino-1 propane sulfonic acid (CAPS) buffer.

Tne labelled proteins in the presence of lanthanide ion exhibited excitation maxima at wavelengths above 300 nm and large Stokes shifts, typically of the order of 300 nm. For example, a solution containing 10 µg/ml labelled goat anti-mouse IgG in the presence of $1\times10^{-5}$M EuCl$_3$ in 0.05M carbonate buffer pH 10, exhibited an excitation maximum at 330 nm and an emission maximum at 616 nm.

Using the methods described above, the fluorescence counts of various proteins labelled with bis(chlorosulfonyl) DPPDA marker was determined using solutions of various concentrations in the ranges indicated in Table 2 below. In each case, a solution in $1\times10^{-5}$M EuCl$_3$ in 0.05M carbonate buffer pH 10 was employed. The results were as indicated in Table 2 below.

TABLE 2

| Protein | Concentrations (ng/ml) | Fluorescence Counts |
| --- | --- | --- |
| Mouse IgG | 2.0 to $10^4$ | 0.079 to 235 |
| Goat anti-mouse IgG | 0.5 to $10^4$ | 0.018 to 471 |
| Goat anti-human IgG | 0.5 to $10^4$ | 0.028 to 140 |

The results indicated that a minimum concentration of about 0.5 ng/ml of the antibody in solution could be detected in each case.

The fluorescence lifetime of DPPDA bis (chlorosulfonyl) labelled mouse IgG—Eu solution was investigated using a 5 µg/ml solution of the labelled mouse IgG containing $1\times10^{-5}$M EuCl$_3$ in 0.05M carbonate pH10, 0.1% SDS with a Perkin-Elmer LS-5 Luminescence Spectrophotometer in the phosphorescence mode. Gating time was set at 0.01 ms and the delay time was varied from 0 to 3 ms in increments of 0.01 ms in the initial stages and 0.02 ms in the later stages. A plot of log luminescence count against delay time was made and the fluorescence lifetime was found to be 700 µs. This showed that the marker protein conjugate chelate was suitable for time-resolved fluorescence immunoassay.

Assay Procedures

The accompanying drawings show graphs evaluating fluorescent immunoassay procedures described in more detail hereinafter, wherein each graph plots log fluorescent count against log concentrations of reagents used in the respective assay procedures, wherein FIGS. 1 and 2 are plots of fluorescent count against labelled mouse IgG antigen concentration;

FIG. 6 is a plot of fluorescent count against labelled BSA antigen concentration.

EXAMPLE 18

Immunofluorometric Assay of Labelled Mouse IgG

The immunological activity of a marker-mouse IgG conjugate prepared as in Example 17 was tested in an immunoreaction between the labelled mouse IgG solutions of varying concentrations and goat anti-mouse IgG coated on polystyrene cuvettes. Bovine serum albumin was used to prevent non specific binding and sodium dodecyl sulfate (SDS) was used to dissociate the antibody-antigen complex after the immunoreaction. SDS causes the proteins to assume unnatural conformations, resulting in migration of the labelled antibody from the surface to the bulk of the solution. The result is a "two-thirds sandwich" immunoassay.

Two milliliters of 10 µg/ml goat anti-mouse IgG in 0.1M carbonate buffer pH 9.5 was placed in each of ten 4 ml polystyrene fluorescence cuvettes (Evergreen). Antibody coating of the plastic surface was allowed to proceed overnight at 4° C. The coated cuvettes were washed twice with a saline solution containing 0.9% NaCl and 0.05% NaN$_3$ and then allowed to stand at 4° C. overnight with 4 ml of a solution containing 0.5% BSA, 0.05M TRIS buffer pH 7.7, 0.9% NaCl and 0.05% NaN$_3$. After two washings with the saline solution, a 2 ml volume of a solution containing labelled mouse IgG in a buffer containing 0.5% BSA, 0.1% Tween 20, 0.05M TRIS pH 7.7, 0.9% NaCl and 0.05% NaN$_3$ was placed in each cuvette. Each cuvette received a solution containing a different concentration of the labelled mouse IgG. The concentrations of the labelled antigen ranged from 0.2 to $10^4$ ng/ml, as indicated by the points plotted in FIG. 1. The labelled mouse IgG was prepared as described in Example 17, using DPPDA bis(chlorosufonyl) in a molar ratio of 100:1 to the mouse IgG. After gentle vortex mixing, the immunoreaction was allowed to proceed for 2 hr at room temperature. The labelled antigen solutions were aspirated and the cuvettes were washed three times with the saline solution. Two millimeters of 0.05M carbonate solution pH 10 containing 0.1% SDS was then shaken in each cuvette to dissociate the antibody-antigen complex. After 1 hr, 20 µl of 0.001M EuCl$_3$ - 0.01M HCl solution was added to each cuvette. The solutions were shaken and the fluorescence counts were measured using a non-gated Perkin-Elmer 650-40 Fluorescence Spectrophotometer with $\lambda_{ex}=330$ nm and $\lambda_{em}=615$ nm and excitation and emission slits at 5 nm and 10 nm, respectively.

Figure 1:
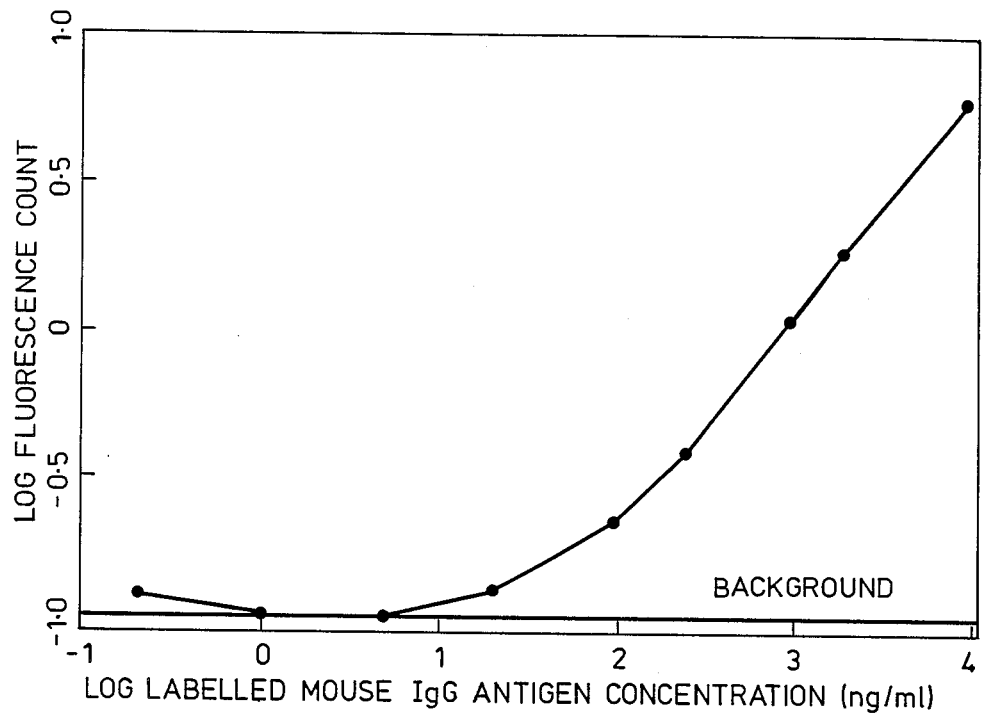

The log fluorescence vs. log concentration (dose-response) plot is shown in FIG. 1. The detection limit for labelled mouse IgG appeared to be 10 ng/ml.

EXAMPLE 19

Immunofluorometric Assay of Labelled Mouse IgG

The procedure of Example 18 was repeated using in place of the labelled mouse IgG solution a labelled mouse IgG solution prepared as described in Example 17 using bis(chlorosulfonyl) DPPDA in a molar ratio of 300:1 to the mouse IgG.

Figure 2:
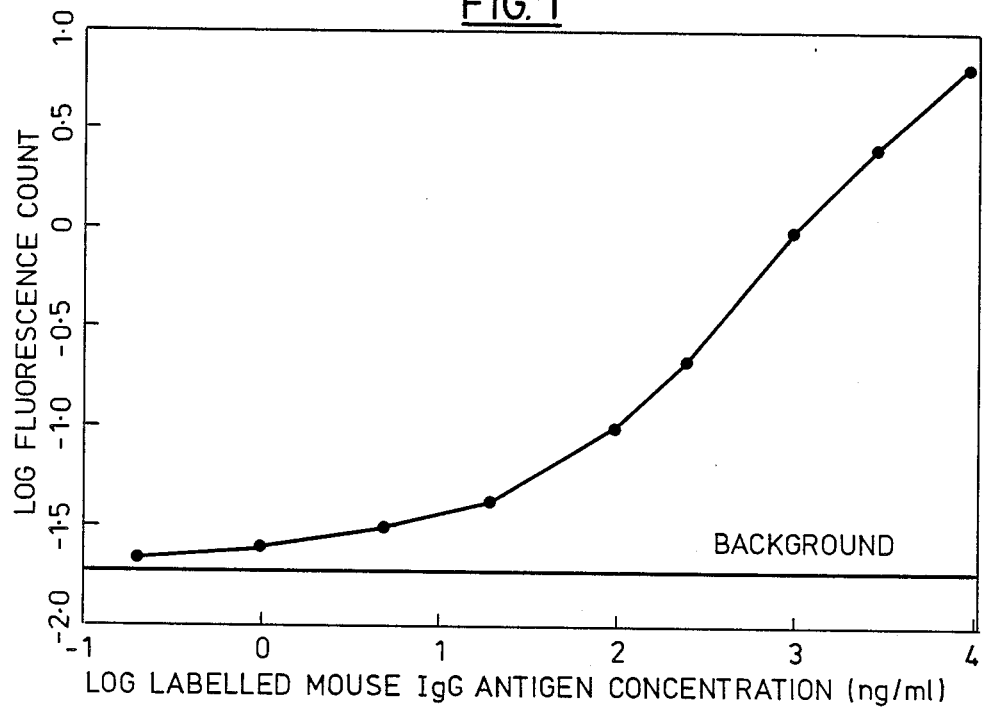

The log fluorescence vs. log concentration (dose response) plot is shown in FIG. 2. The detection limit for labelled mouse IgG appeared to be 1 ng/ml.

EXAMPLE 20

Double Antibody Sandwich Assay

A heterogeneous non competitive double antibody sandwich immunoassay was performed on mouse IgG using marker-labelled goat anti-mouse IgG. The key steps in the assay were as follows: coating of polystyrene cuvettes with unlabelled goat antibody to mouse IgG; coating of the polystyrene surface with BSA to prevent non-specific adsorption; incubation with the mouse IgG antigen; incubation with the labelled goat antibody to mouse IgG; dissociation of the immune complex with SDS; and measurement of fluorescence in solution.

Figure 3:
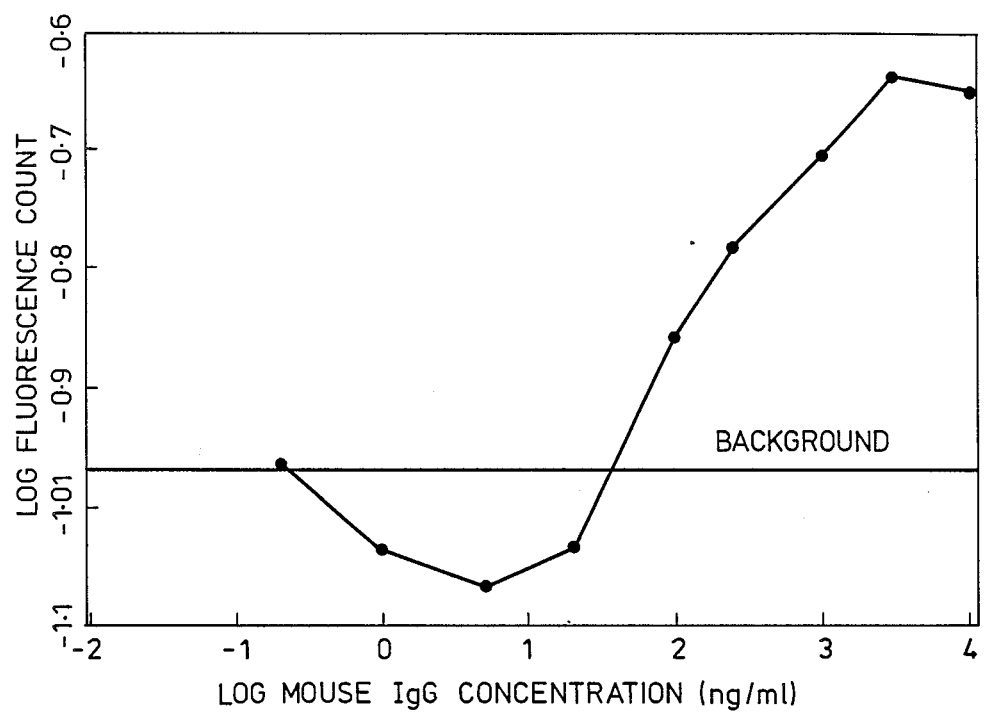
FIG. 3 is a plot of fluorescent count against mouse IgG concentration.

One milliliter of a 10 µg/ml goat antibody to mouse IgG in 0.1M carbonate buffer pH 9.5 was placed in each of ten 4-ml polystyrene fluorescence cuvettes (Evergreen). Antibody coating of the plastic surface was allowed to proceed overnight at 4° C. After two washings with the saline solution, the cuvettes were coated with BSA (1% solution) as described above in Example 19. The cuvettes were then washed twice with the saline solution and then allowed to stand for 2 hr at room temperature with 1 ml mouse IgG antigen solution in a buffer composed of 1% BSA, 0.1% Tween 20, 0.05M TRIS pH 7.7, 0.9% NaCl and 0.05% NaN$_3$. Each cuvette received a solution of different mouse IgG antigen concentration, ranging from 0.2 to 10 ng/ml, as indicated by the points plotted in FIG. 3. After removal of the antigen solutions by aspiration and two saline washings, 1 ml of 1000 ng/ml marker-labelled goat antibody to mouse IgG in the BSA-Tween 20-TRIS-NaCl-NaN$_3$ buffer was allowed to stand in the cuvettes for 2 hr after gentle vortex mixing. The marker-labelled antibody was prepared as described in Example 17, using a molar ratio of DPPDA bis(chlorosulfonyl) DPPDA to the antibody of 100:1. After aspiration of the labelled second antibody solution, 1 ml of 0.1% SDS in 0.05M carbonate buffer pH 10 was shaken in each cuvette to dissociate the immunological complex. After 1 hr, 10 µl of 0.001M EuCl$_3$-0.01M HCl solution was added with vortex mixing. The fluorescence at $\lambda_{ex}=330$ nm and $\lambda_{em}=615$ nm, excitation slit at 5 nm and emission slit at 10 nm, was measured using the non-gated Perkin-Elmer 650-40 Fluorescence Spectrophotometer, and the dose-response plot shown in FIG. 3 was obtained. The limit of detection for this assay was about 50 ng/ml.

EXAMPLE 21

Double Antibody Sandwich Assay

The procedure of Example 20 was repeated using human IgG in place of mouse IgG and goat antibody to human IgG in place of the goat antibody to mouse IgG. The incubation of the coated cuvettes was conducted with solutions of human IgG having concentrations ranging from 0.2 to 10$^4$ ng/ml, as indicated by the points plotted in FIG. 4. The marker-labelled goat antibody to human IgG was prepared as described in Example 9 using a molar ratio of bis(chlorosulfonyl) DPPDA to goat anti-human IgG of 100:1, in carbonate buffer pH 9 at room temperature.

Figure 4:
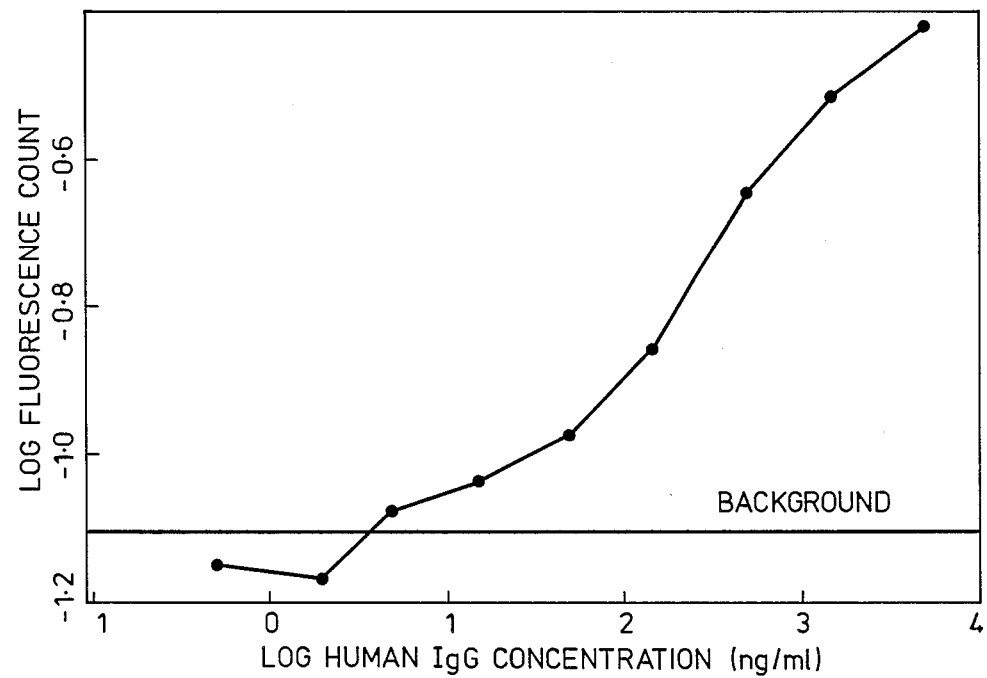
FIGS. 4 and 5 are plots of fluorescent count against human IgG concentration.

The dose response plot obtained is shown in FIG. 4. The limit of detection for immunoglobulins was about 5 ng/ml. In comparison, the limit of detection for immunoglobulins in heterogeneous fluorescent immunoassay using conventional fluorophores, such as fluorescein and rhodamine derivatives, is 200 ng/ml.

EXAMPLE 22

Double Antibody Sandwich Assay

The procedure of Example 21 was repeated using marker-labelled goat antibody to human IgG prepared as described in Example 9, using a molar ratio of bis(chlorosulfonyl) DPPDA to goat antihuman IgG of 200:1 and modified in that the coupling reaction was performed in borate buffer pH 9 in an ice bath.

Figure 5:
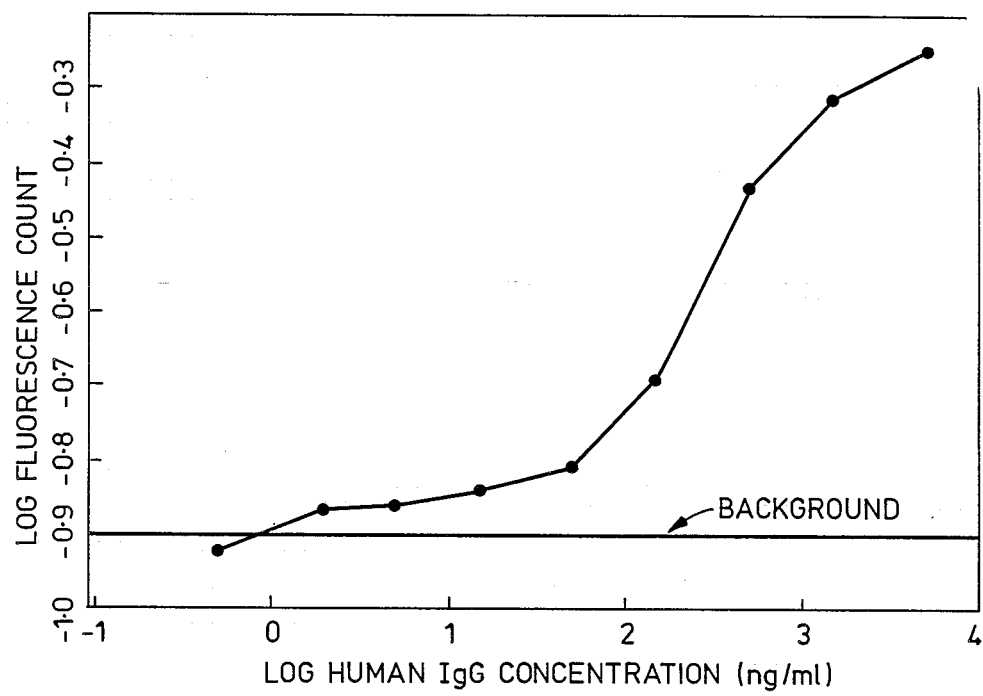

The dose-response plot obtained is shown in FIG. 5. The limit for detection was about 5 ng/ml.

Fluorescence of DPPDA Disulfonate

DPPDA disulfonate (prepared as in Example 15) forms an intensely fluorescent chelate with europium (III) chloride in aqueous solution with excitation and emission maxima at 330 and 617 nm, respectively. The fluorescence of the DPPDA disulfonate-europium solution in carbonate buffer pH 10 is about 2% greater than the fluorescence of DPPDA-europium solution in the same buffer and is linear over five orders of magnitude concentration range. A minimum concentration of $3\times10^{-11}$M DPPDA disulfonate in the presence of $1\times10^{-5}$M EuCl$_3$ could be detected using a non-gated Perkin-Elmer 650-40 Fluorescence Spectrophotometer. Higher sensivitity can be obtained with the use of a gated (time-resolved) fluorometer. The DPPDA disulfonate compound was found to exhibit no ligand-sensitized fluorescence in the presence of terbium (III), samarium (III) and dysprosium (III) salts.

We claim:

1. A regent for fluorescent assay comprising a 1,10-phenanthroline compound selected from the group consisting of compounds of the formula:

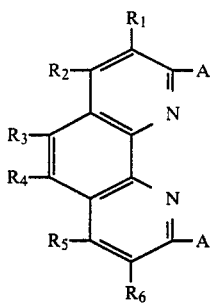

where
A is a C(Z)₃ group in which Z is a halogen;
A is a —COOH group; or
A is a salt, ester or acid halide of —COOH group which readily hydrolyzes to a —COOH group;
wherein $R_1$ to $R_6$ can be hydrogen or another substituent that does not substantially adversely affect the fluorescence properties of lanthanide chelates of the unsubstituted compound; and
at least one $R_1$ to $R_6$ is X— or X—B—, wherein —B— is a divalent aliphatic residue having 1 to 12 carbons, or a divalent carbocyclic or heterocyclic group having 3 to 12 carbons and where X is chosen from the group consisting of M⁺SO₃; wherein said M⁺ is a metal ion not capable of coupling with proteins Y—N₂+—, wherein Y is a monovalent anion; S=C=N—;

ZSO₂—, wherein Z is halogen; HOCH₂CH₂NHSO₂—;

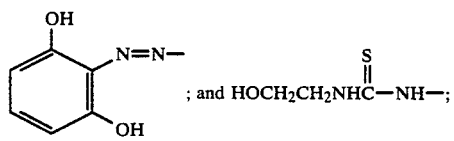

and
each other of $R_1$ to $R_6$ is independently hydrogen, an aliphatic group having 1 to 12 carbons or a carbocylic or heterocyclic group having 3 to 12 carbons wherein $R_1$ to $R_6$ are defined as follows:
$R_3$ and $R_4$ form together with the carbons to which they are attached to a heterocyclic ring group of the formula:

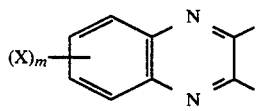

wherein X is defined as above and m is an integer from 1 to 4 and
wherein $R_1$, $R_2$, $R_5$ and $R_6$ are each independently hydrogen, an aliphatic group having 1 to 12 carbons, or a carbocyclic or heterocyclic group having 3 to 12 carbons.

2. A reagent for fluorescent assay comprising a 1,10-phenanthroline compound selected from the group consisting of compounds of the formula:

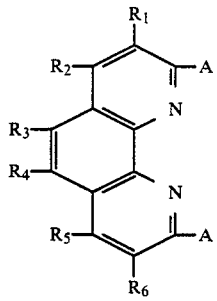

wherein
A is a C(Z)₃ group in which Z is a halogen;
A is a —COOH group; or
A is a salt, ester or acid halide of a —COOH group which readily hydrolyzes to a —COOH group;
wherein $R_1$ to $R_6$ can be hydrogen or another substituent that does not substantially adversely affect the fluorescence properties of lanthanide chelates of the unsubstituted compound; and
at least one of $R_1$ to $R_6$ is X— or X—B—, wherein —B— is a divalent aliphatic residue having 1 to 12 carbons or phenylene; and where X is chosen from the group consisting of M⁺SO₃; wherein said M⁺ is a metal ion not capable of coupling with proteins Y—N₂+—, wherein Y is a monovalent anion; S=C=N—;

ZSO₂—, wherein Z is halogen; HOCH₂CH₂NHSO₂—;

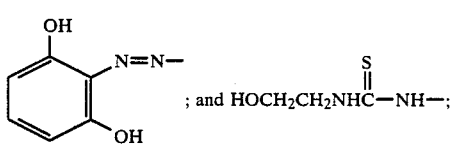

and each other of $R_1$ to $R_6$ is independently hydrogen, an aliphatic group having 1 to 12 carbons or a carbocyclic or heterocyclic group having 3 to 12 carbons.

3. The reagent of claim 1 or 2 wherein said —B— is phenylene.

4. A reagent for fluorescent assay comprising a 1,10-phenanthroline compound selected from the group consisting of compounds of the formula:

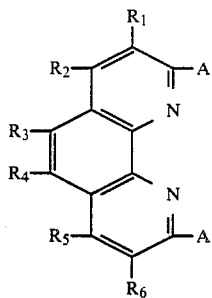

wherein

A is a C(Z)₃ group in which Z is a halogen;

A is a —COOH group; or

A is a salt, ester or acid halid of a —COOH group which readily hydrolyzes to a —COOH group;

wherein R₁ to R₆ can be hydrogen or another substituent that does not substantially adversely affect the fluorescence properties of lanthanide chelates of the unsubstituted compound; and at least one of R₁ to R₆ is X— or,

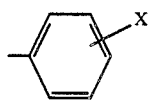

where X is chosen from the group consisting of M⁺SO₃; wherein said M⁺ is a metal ion not capable of coupling with proteins Y—N₂+—, wherein Y is a monovalent anion; S=C=N—;

ZSO₂—, wherein Z is halogen; HOCH₂CH₂NHSO₂—;

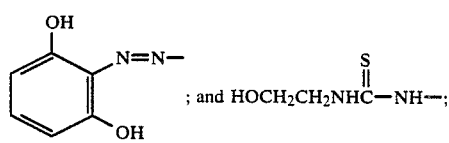
; and HOCH₂CH₂NHC(S)—NH—;

and each other of R₁ to R₆ is independently hydrogen, an aliphatic group having 1 to 12 carbons or a carbocyclic or heterocyclic residue group having 3 to 12 carbons.

5. The reagent of claim 1, 2, or 4 wherein said compound is selected from the group consisting of 4,7-diphenyl-1,10-phenanthroline-2,9-dicarboxylic acid compounds of the formula:

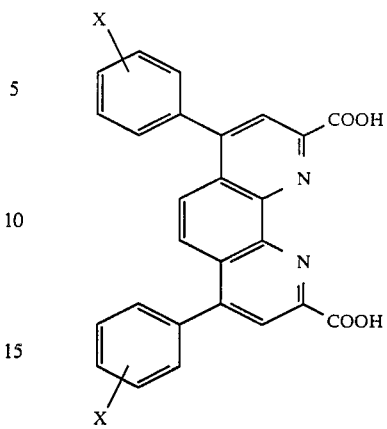

wherein each X is the same or different and has the definition given in claim 1.

6. The reagent of claim 1, 2 or 4, wherein said compound is selected from the group consisting of 4,7-diphenyl-1,10-phenanthroline-2,9dicarboxylic acid compounds of the formula:

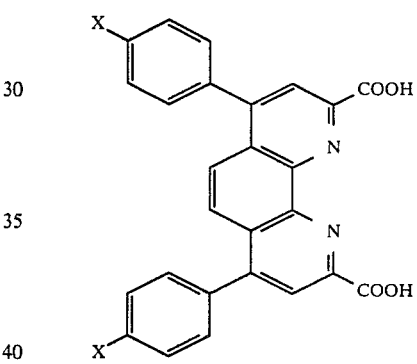

wherein each X is the same or different and has the definition given in claim 1.

7. The reagent of claim 1 wherein said compound is selected from the group consisting of 4,5,9,14-tetraaza-(1,2,3,4)-dibenzanthracene-3,6dicarbocylic acid compounds of the formula:

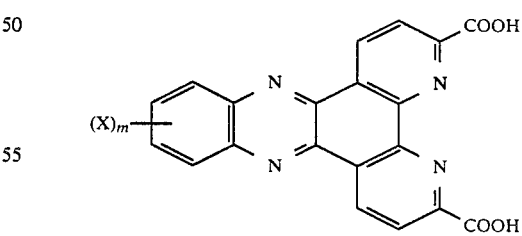

wherein X and m each have the definition given in claim 1.

8. A reagent for fluorescent assay which is a 4,7-bis(-chlorosulfonylphenyl)-1,10-phenanthroline-2,9-dicarboxylic acid.

9. Soluble salts of 4,7-bis(sulfophenyl)-1,10-phenanthroline-2,9dicarboxylic acids.

10. 4,7-diphenyl-1,10-phenanthroline-2,9-dicarboxylic acid.

11. 4,5,9,14-tetraaza-(1,2,3,4,)-dibenzanthracene-3,6-dicarboxylic acid.

12. The compound as in claim 1, 2, 6, 7, which is conjugated to a protein, wherein said protein specifically binds a substance.

13. The reagent of claim 12, wherein said conjugate is bound to a lanthanide metal ion.

14. The reagent of claim 13, wherein said lanthanide metal is selected from the group consisting of europium, terbium, samarium and dysprosium.

15. The reagent of claim 13, wherein said lanthanide metal salt is europium.

16. A method of detecting a substance present in a sample, which comprises:
    (a) contacting said sample with:
        (i) a conjugate of a protein which specifically binds said substance and a lanthanide chelating compound, and
        (ii) a lanthanide metal salt;
    (b) reacting the components of step (a) for a period of time and under conditions sufficient to form a lanthanide complex between said substance, said conjugate, said lanthanide metal salt;
    (c) separately recovering said complex from said sample; and
    (d) determining by fluorometric means the presence of said lanthanide complex;
    wherein said lanthanide chelating compound is:

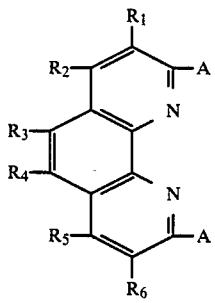

wherein
A is a $C(Z)_3$ group in which Z is a halogen;
A is a —COOH group; or
A is a salt, ester or acid halide of a —COOH group which readily hydrolyzes to a —COOH group;
wherein $R_1$ to $R_6$ can be hydrogen or another substitutent that does not substantially adversely affect the fluorescence properties of lanthanide chelates of the unsubstituted compound; and
at least one of $R_1$ to $R_6$ is X— or X—B—, wherein —B—is a divalent aliphatic residue having 1 to 12 carbons, or a divalent carbocyclic or heterocyclic group having 3 to 12 carbons and where X is chosen from the group consisting of $M^+SO_3$; wherein said $M^+$ is a metal ion not capable of coupling with proteins $Y—N_2+—$, wherein Y is a monovalent anion; S=C=N—;

$ZSO_2—$, wherein Z is halogen; $HOCH_2CH_2NHSO_2—$;

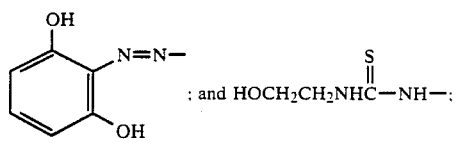

and each other of $R_1$ to $R_6$ is independently hydrogen, an aliphatic group having 1 to 12 carbons or a carbocyclic or heterocyclic group having 3 to 12 carbons or wherein $R_1$ to $R_6$ are defined as follows: $R_3$ and $R_4$ form together with the carbons to which they are attached to a heterocyclic ring group of the formula:

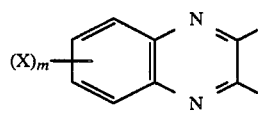

wherein X is defined as above and m is an integer from 1 to 4 and wherein $R_1$, $R_2$, $R_5$ and $R_6$ are each independently hydrogen, an aliphatic group having 1 to 12 carbons, or a carbocyclic or heterocyclic group having 3 to 12 carbons.

17. The method of claim 16 wherein said substance in said sample is immobilized on a solid surface prior to contact with said conjugate, and said complex is separately recovered by adding said lanthanide salt to said sample after said conjugate has bound to said immobilized substance and thereafter removing any unbound conjugate or lanthanide metal salt.

18. The method of claim 16 further including the step of dissociating said bound conjugate from said surface after removal of said unbound conjugate and prior to addition of said lanthanide salt.

19. The method of claim 16 wherein said determination by fluorometric means include the steps of:
    (a) exciting said lanthanide complex with electromagnetic radiation,
    (b) measuring the intensity of emitted fluorescence from said complex, and
    (c) comparing the fluorescence value of step (b) to those samples containing known concentrations of the substance to be determined.

20. A method of detecting a substance present in a sample, which comprises:
    (a) providing a solid surface which specifically binds said substance;
    (b) contacting said sample and said solid surface;
    (c) reacting the components of step (b) for a period of time and under conditions sufficient to bind said substance to said solid surface;
    (d) contacting said solid surface bound substance with a conjugate of a protein which specifically binds said substance and a lanthanide chelating compound;
    (e) separating said conjugate bound to said substance from any unbound conjugate;
    (f) dissociating said bound conjugate from said substance;
    (g) reacting said dissociated conjugate with a lanthanide metal salt to form a lanthanide complex between said conjugate and said lanthanide metal salt;
    (h) determining by fluorometric means the presence of said lanthanide complex;

wherein said lanthanide chelating compound is:

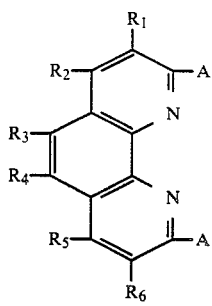

wherein

A is a C(Z)₃ group in which Z is a halogen;

A is a —COOH group; or

A is a salt, ester or acid halide of a —COOH group which readily hydrolyzes to a —COOH group;

wherein $R_1$ to $R_6$ can be hydrogen or another substituent that does not substantially adversely affect the fluorescence properties of lanthanide chelates of the unsubstituted compound; and at least one of $R_1$ to $R_6$ is X— or X—B—, wherein —B— is a divalent aliphatic residue having 1 to 12 carbons, or a divalent carbocyclic or heterocyclic group having 3 to 12 carbons; and where X is chosen from the group consisting of M⁺SO₃; wherein said M⁺ is a metal ion not capable of coupling with proteins Y—N₂+—, wherein Y is a monovalent anion; S=C=N—;

ZSO₂—, wherein Z is halogen; HOCH₂CH₂NHSO₂—;

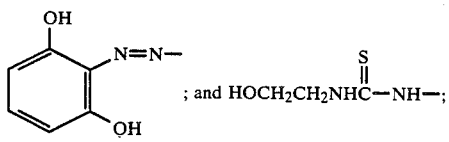

and each other of $R_1$ to $R_6$ is independently hydrogen, an aliphatic group having 1 to 12 carbons or a carbocyclic or heterocyclic group having 3 to 12 carbons or wherein $R_1$ to $R_6$ are defined as follows: $R_3$ and $R_4$ form together with the carbons to which they are attached to a heterocyclic ring group of the formula:

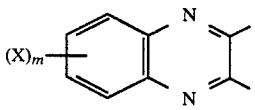

wherein X is defined as above and m is an integer from 1 to 4 and wherein $R_1$, $R_2$, $R_5$ and $R_6$ are each independently hydrogen, an aliphatic group having 1 to 12 carbons, or a carbocyclic or heterocyclic group having 3 to 12 carbons.

21. The method of claim 20, wherein in said step (a) said solid surface has immobilized thereon protein to specifically bind said substance.

22. The method of claim 21, wherein said protein is antibody.

23. The method of claim 16 or 20, wherein said protein in said conjugate is antibody.

24. The method of claim 16 or 20, wherein said lanthanide metal salt is selected from the group consisting of salts of europium, terbium, samarium and dysprosium.

25. The method of claim 16 or 20, wherein said lanthanide metal salt is a europium salt.

26. The method of claim 16, or 20, wherein said substance being detected is selected from the group consisting of an antibody and an antigen.

27. The method of claim 16, or 20, wherein said lanthanide chelating compound is selected from the group consisting of 4,7-diphenyl-1,10-phenanthroline-2,9-dicarboxylic acid compounds of the formula:

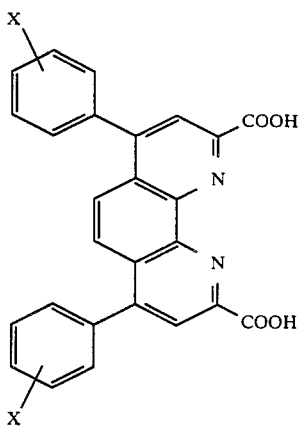

wherein each X is the same or different and has the definition given in claim 1.

28. The method of claim 16, or 20, wherein said lanthanide chelating compound is selected from the group consisting of 4,5,9,14-tetraaza-(1,2,3,4)-dibenzanthracene-3,6-dicarbocylic acid compounds of the formula:

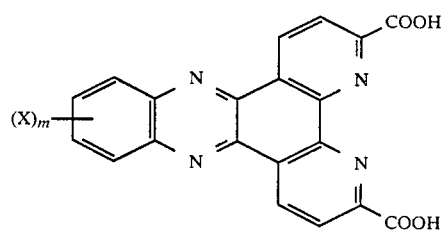

wherein X and m each have the definition given in claim 1.

29. The method of claim 16 or 20, wherein said lanthanide chelating compound is a 4,7-bis(chlorosulfonylphenyl-1,10-phenanthroline-2,9-dicarboxylic acid.

* * * * *